(12) United States Patent
Zhu et al.

(10) Patent No.: US 9,958,379 B1
(45) Date of Patent: *May 1, 2018

(54) CHARACTERIZING OPTICALLY REFLECTIVE FEATURES VIA HYPER-SPECTRAL SENSOR

(71) Applicant: Waymo LLC, Mountain View, CA (US)

(72) Inventors: Jiajun Zhu, Sunnyvale, CA (US); David I. Ferguson, San Francisco, CA (US); Dmitri A. Dolgov, Mountain View, CA (US); Jonathan Baldwin Dowdall, Oakland, CA (US)

(73) Assignee: Waymo LLC, Mountain View, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/955,186

(22) Filed: Dec. 1, 2015

Related U.S. Application Data

(63) Continuation of application No. 13/629,378, filed on Sep. 27, 2012, now Pat. No. 9,234,618.

(51) Int. Cl.
| | |
|---|---|
| *G01C 3/08* | (2006.01) |
| *G01N 21/27* | (2006.01) |
| *G01S 17/08* | (2006.01) |
| *G05D 1/00* | (2006.01) |

(52) U.S. Cl.
CPC .............. *G01N 21/27* (2013.01); *G01S 17/08* (2013.01); *G05D 1/0088* (2013.01)

(58) Field of Classification Search
CPC .......... G01C 3/08; G01C 15/002; G01C 3/04; G01S 17/10; G01S 7/497; G01S 13/865; G01S 13/931; G01B 11/14; G01B 11/24

USPC ............ 356/5.01–5.15, 3.01–3.16, 4.01–4.1
See application file for complete search history.

(56) References Cited

U.S. PATENT DOCUMENTS

| | | | |
|---|---|---|---|
| 4,926,174 | A | 5/1990 | Kelly et al. |
| 5,241,481 | A | 8/1993 | Olsen |
| 6,741,363 | B1 | 5/2004 | Kaupert |
| 7,369,229 | B2 | 5/2008 | Bissett, III et al. |
| 7,502,688 | B2 | 3/2009 | Kirokawa |

(Continued)

OTHER PUBLICATIONS

Hakala et al. 'Full waveform hyperspectral LiDAR for terrestrial laser scanning', Optics Express, vol. 20. No. 7.*

(Continued)

*Primary Examiner* — Assres H Woldemaryam
(74) *Attorney, Agent, or Firm* — McDonnell Boehnen Hulbert & Berghoff LLP

(57) ABSTRACT

A light detection and ranging device associated with an autonomous vehicle scans through a scanning zone while emitting light pulses and receives reflected signals corresponding to the light pulses. The reflected signals indicate a three-dimensional point map of the distribution of reflective points in the scanning zone. A hyperspectral sensor images a region of the scanning zone corresponding to a reflective feature indicated by the three-dimensional point map. The output from the hyperspectral sensor includes spectral information characterizing a spectral distribution of radiation received from the reflective feature. The spectral characteristics of the reflective feature allow for distinguishing solid objects from non-solid reflective features, and a map of solid objects is provided to inform real time navigation decisions.

20 Claims, 12 Drawing Sheets

(56) References Cited

U.S. PATENT DOCUMENTS

| | | | |
|---|---|---|---|
| 8,060,271 | B2 | 11/2011 | Dolgov et al. |
| 8,111,924 | B2 | 2/2012 | Kelle et al. |
| 8,126,642 | B2 | 2/2012 | Trepagnier et al. |
| 8,170,787 | B2 | 5/2012 | Coats et al. |
| 8,743,358 | B2 * | 6/2014 | Treado et al. ............... 356/326 |
| 2004/0130702 | A1 * | 7/2004 | Jupp et al. ................. 356/5.01 |
| 2005/0151965 | A1 * | 7/2005 | Bissett et al. ............... 356/328 |
| 2007/0040121 | A1 | 2/2007 | Kalayeh |
| 2008/0162027 | A1 | 7/2008 | Murphy et al. |
| 2009/0318815 | A1 * | 12/2009 | Barnes et al. ............... 600/473 |
| 2009/0326383 | A1 * | 12/2009 | Barnes et al. ............... 600/476 |
| 2010/0399318 | | 2/2010 | Kmiecik |
| 2010/0104199 | A1 | 4/2010 | Zhang et al. |
| 2010/0118116 | A1 | 5/2010 | Tomasz |
| 2010/0150431 | A1 | 6/2010 | Chen et al. |
| 2010/0198488 | A1 | 8/2010 | Groitzsch et al. |
| 2011/0040482 | A1 | 2/2011 | Brimble et al. |
| 2011/0080306 | A1 | 4/2011 | Leopold et al. |
| 2011/0101239 | A1 * | 5/2011 | Woodhouse et al. ...... 250/458.1 |
| 2011/0274343 | A1 | 11/2011 | Krishnaswamy |
| 2012/0008129 | A1 | 1/2012 | Lu et al. |
| 2012/0044476 | A1 | 2/2012 | Earhart et al. |
| 2012/0292726 | A1 * | 11/2012 | Wallace ....................... 257/432 |
| 2012/0306257 | A1 * | 12/2012 | Silversides et al. ............ 299/18 |

OTHER PUBLICATIONS

Fogler Joseph, 'Multi- and Hyper-Spectral Sensing for Autonomous Ground Vehicle Navigation' , Sandia national Laboratories, 2003.*

Shaw et al., 'Spectral Imaging for Remote Sensing', Lincoln Laboratory Journal, 2003.*

Carswell et al. "Lidar Imagery—From Simple Snapshots to Mobile 3D Panoramas", 2011.*

Cocks et al. "The HYMAPTM Airborne Hyperspectral Sensor: The System, Calibration and Performance", 1998.*

Brook et al., "Fusion of Hyperspectral Images and LiDAR Data for Civil Engineering Structure Monitoring." 2010 2nd Norkshop on Hyperspectral Image and Signal Processing: Evolution in Remote Sensing. IEEE, 2010, 4 pages.

Middleton Research, "Hyperspectral Imaging," Hyperspectral Imaging Catalog, www.middletonresearch.com -etrieved Aug. 2012, pp. 2-4, Middleton, WI.

Middleton Research, "Stages and Scanners," Stages and Scanners Catalog, www.middletonresearch.com, retrieved Aug. 2012, pp. 72-76, Middleton, WI.

Pirozzo et al., "Spectrally Queued Feature Selection for Robotic Visual Odometery." In IS&T/SPIE Electronic Imaging, International Society for Optics and Photonics, Nov. 2010, 12 pages.

* cited by examiner

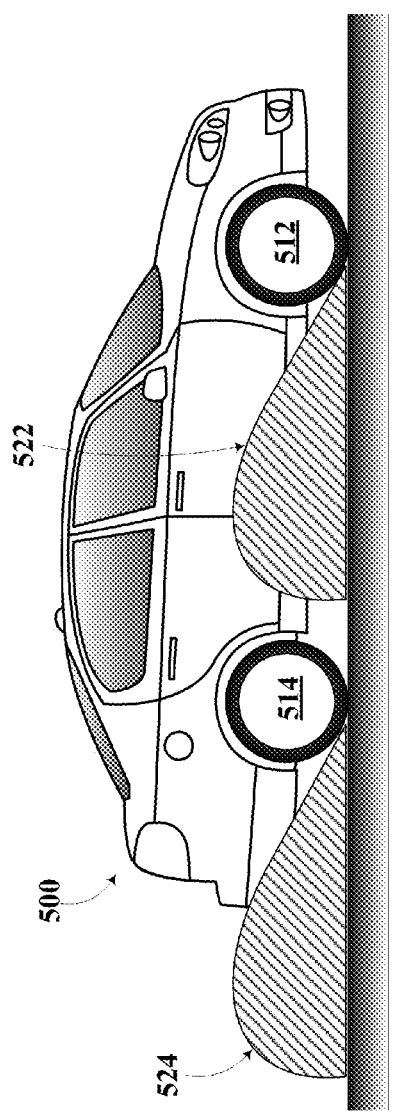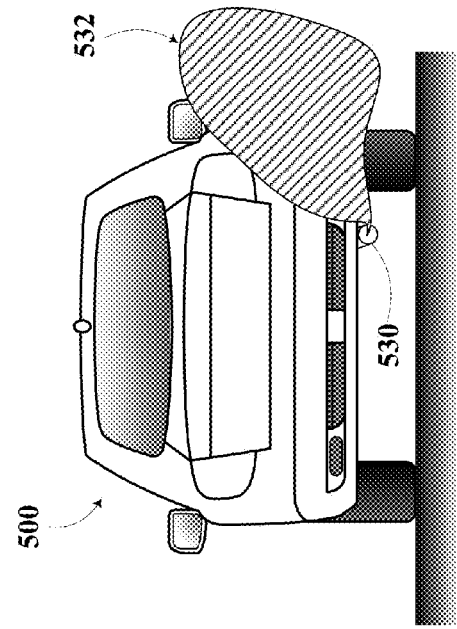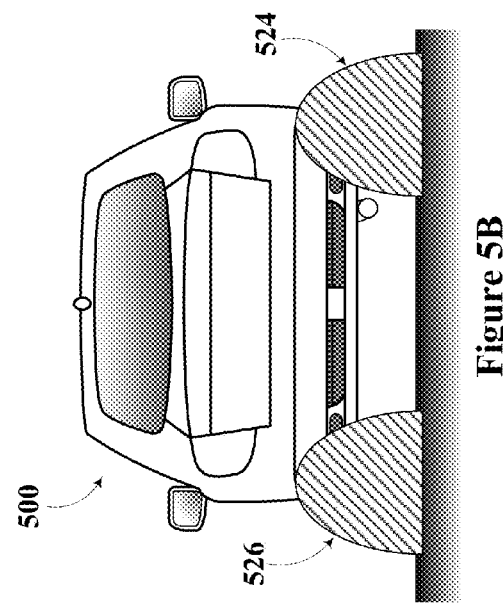
Figure 5A
Figure 5C
Figure 5B

CHARACTERIZING OPTICALLY REFLECTIVE FEATURES VIA HYPER-SPECTRAL SENSOR

CROSS-REFERENCE TO RELATED APPLICATIONS

The present application is a continuation patent application claiming priority to U.S. application Ser. No. 13/629,378 filed Sep. 27, 2012, the contents of which are hereby incorporated by reference.

BACKGROUND

Unless otherwise indicated herein, the materials described in this section are not prior art to the claims in this application and are not admitted to be prior art by inclusion in this section.

Vehicles can be configured to operate in an autonomous mode in which the vehicle navigates through an environment with little or no input from a driver. Such autonomous vehicles can include one or more sensors that are configured to detect information about the environment in which the vehicle operates. The vehicle and its associated computer-implemented controller use the detected information to navigate through the environment. For example, if the sensor(s) detect that the vehicle is approaching an obstacle, as determined by the computer-implemented controller, the controller adjusts the vehicle's directional controls to cause the vehicle to navigate around the obstacle.

One such sensor is a light detection and ranging (LIDAR) device. A LIDAR actively estimates distances to environmental features while scanning through a scene to assemble a cloud of point positions indicative of the three-dimensional shape of the environmental scene. Individual points are measured by generating a laser pulse and detecting a returning pulse, if any, reflected from an environmental object, and determining the distance to the reflective object according to the time delay between the emitted pulse and the reception of the reflected pulse. The laser, or set of lasers, can be rapidly and repeatedly scanned across a scene to provide continuous real-time information on distances to reflective objects in the scene. Combining the measured distances and the orientation of the laser(s) while measuring each distance allows for associating a three-dimensional position with each returning pulse. A three-dimensional map of points of reflective features is generated based on the returning pulses for the entire scanning zone. The three-dimensional point map thereby indicates positions of reflective objects in the scanned scene.

A hyperspectral sensor is a spectral analysis tool that captures an image with detailed spectral information of the scene on a pixelated basis. Rather than representing an image with red, green, and blue color content information for each pixel, each pixel can include a power spectral density values for a series of wavelength ranges. For instance, a hyperspectral sensor may generate 320×460 pixel images, with sensitivity to a range of wavelengths spanning 1000 nm and a resolution of about 4 nm. The data generated from such an image can be considered a cube of data values, with 320 by 460 length and width (pixelated image size) and 250 height (1000 nm/4 nm). By providing spectral information for spatially distinct regions of an image, distinct materials can be identified according to their characteristic spectral transmission and/or reflection "fingerprints."

Some hyperspectral imagers are scanned across a scene while simultaneously taking spectra for a line of pixels. For example, received light is passed through a slit to select a single "line" of a scene being imaged. The slit of light is passed through a diffraction grating, to redirect the light according to wavelength and the diffracted pattern is passed to an imaging focal plane, where a detector characterizes the spectral content at each spectral band. Sweeping the hyperspectral sensor across a scene transverse to the elongated direction of the slit allows for gradually developing a two-dimensional picture of a scene. In another example, a series of images of a scene is captured while an adjustable filter is incrementally adjusted between each image to select for each wavelength band of interest. Each image then provides the spectral content of a scene at the particular spectral band selected for.

SUMMARY

An environmental sensor system for an autonomous vehicle is disclosed that combines information from a LIDAR device and a hyperspectral sensor to determine whether features indicated by the LIDAR device include solid materials. The hyperspectral sensor is used to identify material compositions according to spectral fingerprints, and thereby distinguish solid materials from fluid materials, such as exhaust plumes, water vapor, etc. The ability to distinguish solid materials from fluid materials allows the autonomous vehicle to inform navigation decisions on the basis of the environmental surroundings determined to include solid materials while safely ignoring fluid materials that do not present navigational obstacles, such as exhaust plumes, water vapor, etc.

Some embodiments of the present disclosure provide a method including scanning a light detection and ranging (LIDAR) device associated with an autonomous vehicle through a scanning zone while emitting light pulses. The method can also include determining a three-dimensional (3-D) point map of the scanning zone based on time delays between emitting the light pulses and receiving corresponding returning reflected signals and based on orientations of the LIDAR device while emitting the light pulses. The method can also include imaging, with a hyperspectral sensor associated with the autonomous vehicle, a region of the scanning zone corresponding to a reflective feature indicated by the 3-D point map so as to generate spectral information characterizing a spectral distribution of radiation received from the reflective feature. The method can also include analyzing the spectral information to determine whether the reflective feature includes a solid material. The method can also include controlling the autonomous vehicle to avoid reflective features determined to include a solid material without avoiding reflective features determined to not include a solid material.

Some embodiments of the present disclosure provide an autonomous vehicle system. The autonomous vehicle system can include a light detection and ranging (LIDAR) device including: a light source configured to be scanned through a scanning zone while emitting light pulses; and a light detector configured to receive returning reflected signals from reflective features in the scanning zone, if any. The autonomous vehicle system can include a hyperspectral sensor configured to image selected regions of the scanning zone and to characterize spectral distributions of radiation received from the imaged regions. The autonomous vehicle can also include a controller configured to instruct the LIDAR device to scan the scanning zone while emitting light pulses. The controller can also be configured to receive information from the LIDAR device indicative of the time delays between the emission of the light pulses and the reception of corresponding returning reflected signals. The controller can also be configured to determine, based on the time delays and orientations of the LIDAR device while emitting the light pulses, a three dimensional (3-D) point map. The controller can also be configured to instruct the hyperspectral sensor to image a region of the scanning zone corresponding to a reflective feature indicated by the 3-D point map. The controller can also be configured to receive from the hyperspectral sensor spectral information characterizing a spectral distribution of radiation received from the reflective feature. The controller can also be configured to determine whether the reflective feature includes a solid material based on the spectral information. The controller can also be configured to control the autonomous vehicle to avoid reflective features determined to include a solid material without avoiding reflective features determined to not include a solid material.

Some embodiments of the present disclosure provide a computer readable medium storing instructions that, when executed by one or more processors in a computing device, cause the computing device to perform operations including scanning a light detection and ranging (LIDAR) device associated with an autonomous vehicle through a scanning zone while emitting light pulses. The operations can also include determining a three-dimensional (3-D) point map of the scanning zone based on time delays between emitting the light pulses and receiving corresponding returning reflected signals and based on orientations of the LIDAR device while emitting the light pulses. The operations can also include imaging, with a hyperspectral sensor associated with the autonomous vehicle, a region of the scanning zone corresponding to a reflective feature indicated by the 3-D point map so as to generate spectral information characterizing a spectral distribution of radiation received from the reflective feature. The operations can also include analyzing the spectral information to determine whether the reflective feature includes a solid material. The operations can also include controlling the autonomous vehicle to avoid reflective features determined to include a solid material without avoiding reflective features determined to not include a solid material.

These as well as other aspects, advantages, and alternatives, will become apparent to those of ordinary skill in the art by reading the following detailed description, with reference where appropriate to the accompanying drawings.

BRIEF DESCRIPTION OF THE FIGURES

FIG. 5A is a side view of a car driving on wet pavement so as to generate a distribution of water trailing each wheel.

FIG. 5B is a back view of a car driving on wet pavement so as to generate a distribution of water trailing each wheel.

FIG. 5C is a back view of a car emitting a plume of exhaust gas from a rear tail pipe.

DETAILED DESCRIPTION

Figure 1:
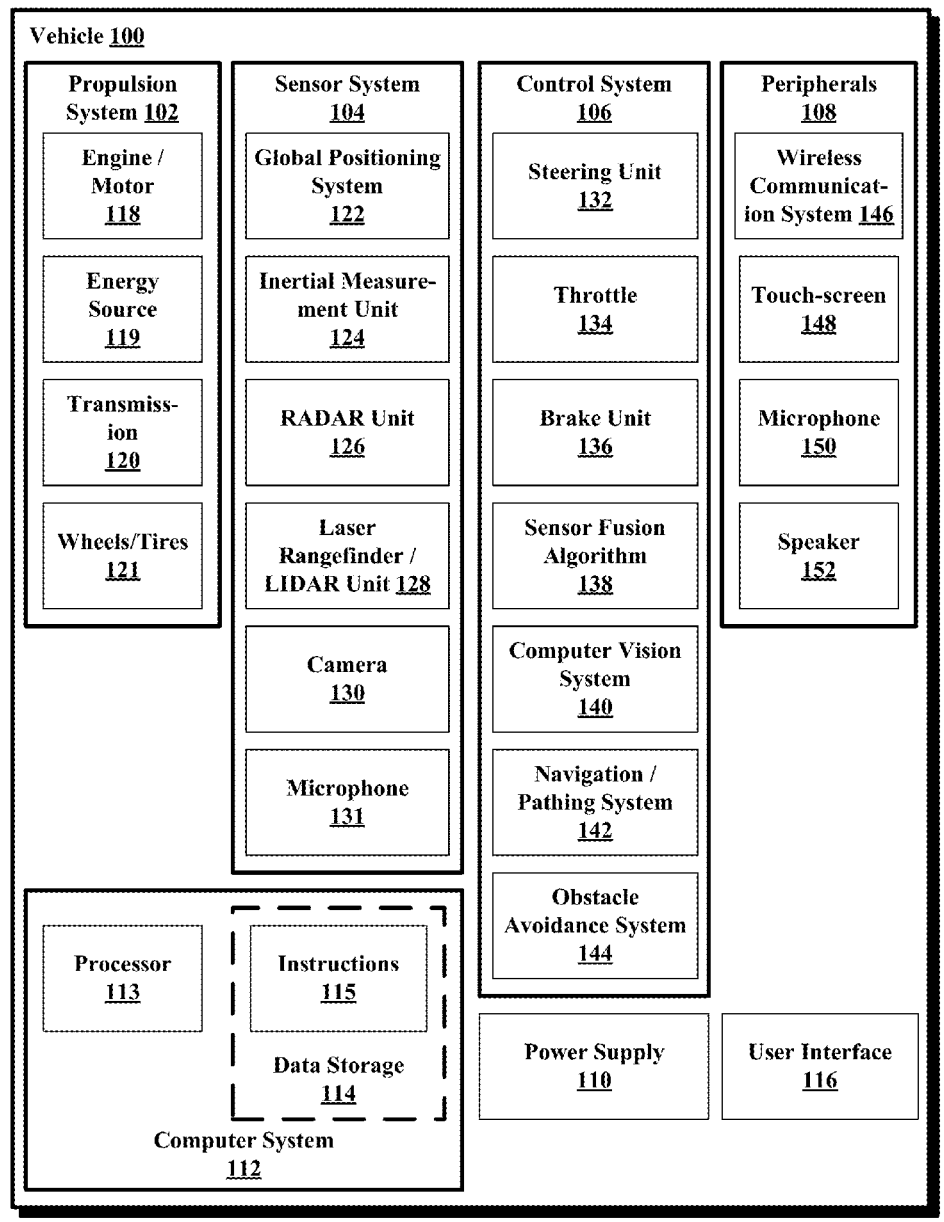
FIG. 1 is a functional block diagram depicting aspects of an autonomous vehicle.

Example embodiments relate to an autonomous vehicle, such as a driverless automobile, that includes a light detection and ranging (LIDAR) sensor for actively detecting reflective features in the environment surrounding the vehicle. A controller analyzes information from the LIDAR sensor to identify the surroundings of the vehicle. The controller determines how to direct the propulsion systems of the vehicle to effect a navigation path that substantially avoids obstacles indicated by the information from the LIDAR sensor.

Each distance measurement of a scanning LIDAR is associated with a point or "spot" on a reflective feature in the environment surrounding the LIDAR from which an emitted pulse is reflected. Scanning the LIDAR through a range of orientations provides a three-dimensional distribution of reflective points, which is referred to herein as a 3-D point map or 3-D point cloud. Spatial features that appear in a 3-D point map generally correspond to objects detected by laser pulses from the LIDAR that bounce off the objects' surfaces. In generating such a 3-D point map, it may not be possible for a conventional LIDAR to determine the physical nature of a detected object, other than the object's distance and shape as revealed by the laser light that bounces off the object's surface and is detected as return pulses. In particular, an object detected by a conventional scanning LIDAR and appearing as a feature in a 3-D point map may not have a solid surface, or even any solid portions within its volume. For example, a cloud of exhaust gas or aggregate drops of water in rain or in a splash of water from a puddle may be detected by a LIDAR and appear in a 3-D point map with either a well-defined shape, or an amorphous shape. Thus, a LIDAR detector is sensitive to non-solid reflective features, even though such features may be safely disregarded for object avoidance and/or navigational purposes of the autonomous vehicle.

For some applications of a scanning LIDAR, it may be necessary or desirable to be able to distinguish between spatial features in a 3-D point map that correspond to detected objects that are at least partially solid and detected objects that are not. For example, a 3-D point map may serve as real-time input to an application and/or system that guides a moving vehicle through a region that may contain physical objects or obstacles in the vehicle's path. In such a situation, safe navigation of the vehicle through the region can depend on avoiding objects that represent collision hazards, such as solid objects, while minimizing or eliminating maneuvers around non-solid reflective features that correspond to objects or materials that could otherwise be safely passed through.

Without the ability to distinguish between solid reflective features and non-solid reflective features, autonomous vehicles can make undesirable maneuvers to the detriment of passenger safety, fuel economy, etc. For example, in cold weather, the exhaust of a car within the scanning zone of the LIDAR can appear reflective, and cause an automatic object avoidance system to unnecessarily maneuver the vehicle around the exhaust. Similarly, during a rainfall, water on the road surface might be thrown up and back by the wheels of a car in the scanning zone of the LIDAR, forming a spray pattern appearing as a lobe or tail trailing each wheel of other cars on the road. The lobe or tail can then be detected by the LIDAR and cause an automatic object avoidance system to unnecessarily maneuver the vehicle to avoid the splashing water, even though such maneuvers are not warranted by a collision hazard.

In some embodiments, a processor-based system including a scanning LIDAR and a hyperspectral sensor device use the hyperspectral sensor to spectrally characterize regions of the scanning zone in real time. Reflective features indicated by the LIDAR are then determined to be either solid or not solid based on their spectral features. The hyperspectral sensor can measure incoming radiation over one or more spectral ranges and detect spectral content in multiple spectral bands to identify spectral features such as absorption and/or emission lines that characterize particular materials. Various spectral features can be identified with physical characteristics of matter, including chemical composition and physical state (e.g., gaseous, liquid, solid). For example, spectral profiling via a hyperspectral sensor can be used to identify water, carbon dioxide, and carbon monoxide, and further can be used to determine whether the identified matter is solid, liquid, or gaseous. Spectral features can include emission lines, absorption lines, characteristic spectral shapes, and relative strengths of two or more portions of a spectrum, among others. Spectral analysis of spatial features detected in a 3-D point map generated by the LIDAR can thereby be used to determine whether or not the spatial features in the 3-D point map correspond to solid objects. Such a determination can thus be used to distinguish reflective features in the 3-D point map that are solid from reflective features that are not solid.

In example embodiments, a hyperspectral sensor device can include a camera with an imaging component, such as a charge-coupled device (CCD), which produces images in a pixel array. Spectral analysis may be carried out on a pixel-by-pixel basis, allowing results of the spectral analysis to be located within the field of view covered by the pixel array of the hyperspectral sensor. Thus, physical characteristics of objects observed by the hyperspectral sensor, as revealed via spectral analysis, can be associated with spatial location. By correlating the locations of spatial features seen in a 3-D point map generated by the scanning LIDAR with corresponding locations in the pixel array of the hyperspectral sensor, spectral analysis can be directed to the spatial features, thereby helping to ensure that the hyperspectral sensor's capability to distinguish between solid, liquid, and gaseous matter is applied to relevant or appropriate spatial regions within the field of view.

In example embodiments, spectral analysis with the hyperspectral sensor can be carried out in response to determining presence and location of a spatial feature or features in the 3-D point map. For example, once the presence of a spatial feature in the 3-D point map is determined, spectral analysis with the hyperspectral sensor can be triggered or invoked. The location of the spatial feature in the 3-D point map could be used to determine where the spatial feature would be located in the pixel array of the hyperspectral sensor. The spectral analysis of the pixels associated with the location in the hyperspectral sensor can then be used to determine if the object or material corresponding to the spatial feature is solid, liquid, or gaseous. The spectral analysis can also be used to determine the chemical or physical composition of the reflective feature.

Additionally or alternatively, spectral analysis with the hyperspectral sensor could be carried out routinely during operation of the scanning LIDAR. In this case, the location of a spatial feature in the 3-D point map can still be used to determine where in the pixel array of the hyperspectral sensor the spatial feature is located.

In example embodiments, two (or more) hyperspectral sensors (or more limited spectral analysis devices) can be used in order to provide a stereoscopic spatial view of a region corresponding to a LIDAR scanning zone. An arrangement with multiple hyperspectral sensors can be useful or desirable, for example, to achieve a more accurate spatial localization of a spectral analysis of spatial feature in a 3-D point map. For instance, a single pixel array of a hyperspectral sensor can allow localization only within a two-dimensional field of view of the image plane, which might not be sufficient or desirable in some cases. By using two hyperspectral sensors, each having a distinct image plane, a 3-D (stereoscopic) view can be achieved that provides more accurate correlation of a spatial feature in a LIDAR indicated 3-D point map with a corresponding feature viewed by the hyperspectral sensor(s).

In example embodiments, the example system may include one or more processors, one or more forms of memory, one or more input devices/interfaces, one or more output devices/interfaces, and machine-readable instructions that when executed by the one or more processors cause the system to carry out the various functions, tasks, capabilities, etc., described above.

Some aspects of the example methods described herein may be carried out in whole or in part by an autonomous vehicle or components thereof. However, some example methods may also be carried out in whole or in part by a system or systems that are remote from an autonomous vehicle. For instance, an example method could be carried out in part or in full by a server system, which receives information from sensors (e.g., raw sensor data and/or information derived therefrom) of an autonomous vehicle. Other examples are also possible.

Example systems within the scope of the present disclosure will now be described in greater detail. An example system may be implemented in, or may take the form of, an automobile. However, an example system may also be implemented in or take the form of other vehicles, such as cars, trucks, motorcycles, buses, boats, airplanes, helicopters, lawn mowers, earth movers, boats, snowmobiles, aircraft, recreational vehicles, amusement park vehicles, farm equipment, construction equipment, trams, golf carts, trains, and trolleys. Other vehicles are possible as well.

FIG. 1 is a functional block diagram illustrating a vehicle 100 according to an example embodiment. The vehicle 100 is configured to operate fully or partially in an autonomous mode, and thus may be referred to as an "autonomous vehicle." For example, a computer system 112 can control the vehicle 100 while in an autonomous mode via control instructions to a control system 106 for the vehicle 100. The computer system 112 can receive information from one or more sensor systems 104, and base one or more control processes (such as setting a heading so as to avoid a detected obstacle) upon the received information in an automated fashion.

The autonomous vehicle 100 can be fully autonomous or partially autonomous. In a partially autonomous vehicle some functions can optionally be manually controlled (e.g., by a driver) some or all of the time. Further, a partially autonomous vehicle can be configured to switch between a fully-manual operation mode and a partially-autonomous and/or a fully-autonomous operation mode.

The vehicle 100 includes a propulsion system 102, a sensor system 104, a control system 106, one or more peripherals 108, a power supply 110, a computer system 112, and a user interface 116. The vehicle 100 may include more or fewer subsystems and each subsystem can optionally include multiple components. Further, each of the subsystems and components of vehicle 100 can be interconnected and/or in communication. Thus, one or more of the functions of the vehicle 100 described herein can optionally be divided between additional functional or physical components, or combined into fewer functional or physical components. In some further examples, additional functional and/or physical components may be added to the examples illustrated by FIG. 1.

The propulsion system 102 can include components operable to provide powered motion to the vehicle 100. In some embodiments the propulsion system 102 includes an engine/motor 118, an energy source 119, a transmission 120, and wheels/tires 121. The engine/motor 118 converts energy source 119 to mechanical energy. In some embodiments, the propulsion system 102 can optionally include one or both of engines and/or motors. For example, a gas-electric hybrid vehicle can include both a gasoline/diesel engine and an electric motor.

The energy source 119 represents a source of energy, such as electrical and/or chemical energy, that may, in full or in part, power the engine/motor 118. That is, the engine/motor 118 can be configured to convert the energy source 119 to mechanical energy to operate the transmission. In some embodiments, the energy source 119 can include gasoline, diesel, other petroleum-based fuels, propane, other compressed gas-based fuels, ethanol, solar panels, batteries, capacitors, flywheels, regenerative braking systems, and/or other sources of electrical power, etc. The energy source 119 can also provide energy for other systems of the vehicle 100.

The transmission 120 includes appropriate gears and/or mechanical elements suitable to convey the mechanical power from the engine/motor 118 to the wheels/tires 121. In some embodiments, the transmission 120 includes a gearbox, a clutch, a differential, a drive shaft, and/or axle(s), etc.

The wheels/tires 121 are arranged to stably support the vehicle 100 while providing frictional traction with a surface, such as a road, upon which the vehicle 100 moves. Accordingly, the wheels/tires 121 are configured and arranged according to the nature of the vehicle 100. For example, the wheels/tires can be arranged as a unicycle, bicycle, motorcycle, tricycle, or car/truck four-wheel format. Other wheel/tire geometries are possible, such as those including six or more wheels. Any combination of the wheels/tires 121 of vehicle 100 may be operable to rotate differentially with respect to other wheels/tires 121. The wheels/tires 121 can optionally include at least one wheel that is rigidly attached to the transmission 120 and at least one tire coupled to a rim of a corresponding wheel that makes contact with a driving surface. The wheels/tires 121 may include any combination of metal and rubber, and/or other materials or combination of materials.

The sensor system 104 generally includes one or more sensors configured to detect information about the environment surrounding the vehicle 100. For example, the sensor system 104 can include a Global Positioning System (GPS) 122, an inertial measurement unit (IMU) 124, a RADAR unit 126, a laser rangefinder/LIDAR unit 128, a camera 130, and/or a microphone 131. The sensor system 104 could also include sensors configured to monitor internal systems of the vehicle 100 (e.g., $O_2$ monitor, fuel gauge, engine oil temperature, wheel speed sensors, etc.). One or more of the sensors included in sensor system 104 could be configured to be actuated separately and/or collectively in order to modify a position and/or an orientation of the one or more sensors.

The GPS 122 is a sensor configured to estimate a geographic location of the vehicle 100. To this end, GPS 122 can include a transceiver operable to provide information regarding the position of the vehicle 100 with respect to the Earth.

The IMU 124 can include any combination of sensors (e.g., accelerometers and gyroscopes) configured to sense position and orientation changes of the vehicle 100 based on inertial acceleration.

The RADAR unit 126 can represent a system that utilizes radio signals to sense objects within the local environment of the vehicle 100. In some embodiments, in addition to sensing the objects, the RADAR unit 126 and/or the computer system 112 can additionally be configured to sense the speed and/or heading of the objects.

Similarly, the laser rangefinder or LIDAR unit 128 can be any sensor configured to sense objects in the environment in which the vehicle 100 is located using lasers. The laser rangefinder/LIDAR unit 128 can include one or more laser sources, a laser scanner, and one or more detectors, among other system components. The laser rangefinder/LIDAR unit 128 can be configured to operate in a coherent (e.g., using heterodyne detection) or an incoherent detection mode.

The camera 130 can include one or more devices configured to capture a plurality of images of the environment surrounding the vehicle 100. The camera 130 can be a still camera or a video camera. In some embodiments, the camera 130 can be mechanically movable such as by rotating and/or tilting a platform to which the camera is mounted. As such, a control process of vehicle 100 may be implemented to control the movement of camera 130.

The sensor system 104 can also include a microphone 131. The microphone 131 can be configured to capture sound from the environment surrounding vehicle 100. In some cases, multiple microphones can be arranged as a microphone array, or possibly as multiple microphone arrays.

The control system 106 is configured to control operation(s) regulating acceleration of the vehicle 100 and its components. To effect acceleration, the control system 106 includes a steering unit 132, throttle 134, brake unit 136, a sensor fusion algorithm 138, a computer vision system 140, a navigation/pathing system 142, and/or an obstacle avoidance system 144, etc.

The steering unit 132 is operable to adjust the heading of vehicle 100. For example, the steering unit can adjust the axis (or axes) of one or more of the wheels/tires 121 so as to effect turning of the vehicle. The throttle 134 is configured to control, for instance, the operating speed of the engine/motor 118 and, in turn, adjust forward acceleration of the vehicle 100 via the transmission 120 and wheels/tires 121. The brake unit 136 decelerates the vehicle 100. The brake unit 136 can use friction to slow the wheels/tires 121. In some embodiments, the brake unit 136 inductively decelerates the wheels/tires 121 by a regenerative braking process to convert kinetic energy of the wheels/tires 121 to electric current.

The sensor fusion algorithm 138 is an algorithm (or a computer program product storing an algorithm) configured to accept data from the sensor system 104 as an input. The data may include, for example, data representing information sensed at the sensors of the sensor system 104. The sensor fusion algorithm 138 can include, for example, a Kalman filter, Bayesian network, etc. The sensor fusion algorithm 138 provides assessments regarding the environment surrounding the vehicle based on the data from sensor system 104. In some embodiments, the assessments can include evaluations of individual objects and/or features in the environment surrounding vehicle 100, evaluations of particular situations, and/or evaluations of possible interference between the vehicle 100 and features in the environment (e.g., such as predicting collisions and/or impacts) based on the particular situations.

The computer vision system 140 can process and analyze images captured by camera 130 to identify objects and/or features in the environment surrounding vehicle 100. The detected features/objects can include traffic signals, road way boundaries, other vehicles, pedestrians, and/or obstacles, etc. The computer vision system 140 can optionally employ an object recognition algorithm, a Structure From Motion (SFM) algorithm, video tracking, and/or available computer vision techniques to effect categorization and/or identification of detected features/objects. In some embodiments, the computer vision system 140 can be additionally configured to map the environment, track perceived objects, estimate the speed of objects, etc.

The navigation and pathing system 142 is configured to determine a driving path for the vehicle 100. For example, the navigation and pathing system 142 can determine a series of speeds and directional headings to effect movement of the vehicle along a path that substantially avoids perceived obstacles while generally advancing the vehicle along a roadway-based path leading to an ultimate destination, which can be set according to user inputs via the user interface 116, for example. The navigation and pathing system 142 can additionally be configured to update the driving path dynamically while the vehicle 100 is in operation on the basis of perceived obstacles, traffic patterns, weather/road conditions, etc. In some embodiments, the navigation and pathing system 142 can be configured to incorporate data from the sensor fusion algorithm 138, the GPS 122, and one or more predetermined maps so as to determine the driving path for vehicle 100.

The obstacle avoidance system 144 can represent a control system configured to identify, evaluate, and avoid or otherwise negotiate potential obstacles in the environment surrounding the vehicle 100. For example, the obstacle avoidance system 144 can effect changes in the navigation of the vehicle by operating one or more subsystems in the control system 106 to undertake swerving maneuvers, turning maneuvers, braking maneuvers, etc. In some embodiments, the obstacle avoidance system 144 is configured to automatically determine feasible ("available") obstacle avoidance maneuvers on the basis of surrounding traffic patterns, road conditions, etc. For example, the obstacle avoidance system 144 can be configured such that a swerving maneuver is not undertaken when other sensor systems detect vehicles, construction barriers, other obstacles, etc. in the region adjacent the vehicle that would be swerved into. In some embodiments, the obstacle avoidance system 144 can automatically select the maneuver that is both available and maximizes safety of occupants of the vehicle. For example, the obstacle avoidance system 144 can select an avoidance maneuver predicted to cause the least amount of acceleration in a passenger cabin of the vehicle 100.

The vehicle 100 also includes peripherals 108 configured to allow interaction between the vehicle 100 and external sensors, other vehicles, other computer systems, and/or a user, such as an occupant of the vehicle 100. For example, the peripherals 108 for receiving information from occupants, external systems, etc. can include a wireless communication system 146, a touchscreen 148, a microphone 150, and/or a speaker 152.

In some embodiments, the peripherals 108 function to receive inputs for a user of the vehicle 100 to interact with the user interface 116. To this end, the touchscreen 148 can both provide information to a user of vehicle 100, and convey information from the user indicated via the touchscreen 148 to the user interface 116. The touchscreen 148 can be configured to sense both touch positions and touch gestures from a user's finger (or stylus, etc.) via capacitive sensing, resistance sensing, optical sensing, a surface acoustic wave process, etc. The touchscreen 148 can be capable of sensing finger movement in a direction parallel or planar to the touchscreen surface, in a direction normal to the touchscreen surface, or both, and may also be capable of sensing a level of pressure applied to the touchscreen surface. An occupant of the vehicle 100 can also utilize a voice command interface. For example, the microphone 150 can be configured to receive audio (e.g., a voice command or other audio input) from a user of the vehicle 100. Similarly, the speakers 152 can be configured to output audio to the user of the vehicle 100.

In some embodiments, the peripherals 108 function to allow communication between the vehicle 100 and external systems, such as devices, sensors, other vehicles, etc. within its surrounding environment and/or controllers, servers, etc., physically located far from the vehicle that provide useful information regarding the vehicle's surroundings, such as traffic information, weather information, etc. For example, the wireless communication system 146 can wirelessly communicate with one or more devices directly or via a communication network. The wireless communication system 146 can optionally use 3G cellular communication, such as CDMA, EVDO, GSM/GPRS, and/or 4G cellular communication, such as WiMAX or LTE. Additionally or alternatively, wireless communication system 146 can communicate with a wireless local area network (WLAN), for example, using WiFi. In some embodiments, wireless communication system 146 could communicate directly with a device, for example, using an infrared link, Bluetooth, and/or ZigBee. The wireless communication system 146 can include one or more dedicated short range communication (DSRC) devices that can include public and/or private data communications between vehicles and/or roadside stations. Other wireless protocols for sending and receiving information embedded in signals, such as various vehicular communication systems, can also be employed by the wireless communication system 146 within the context of the present disclosure.

As noted above, the power supply 110 can provide power to components of vehicle 100, such as electronics in the peripherals 108, computer system 112, sensor system 104, etc. The power supply 110 can include a rechargeable lithium-ion or lead-acid battery for storing and discharging electrical energy to the various powered components, for example. In some embodiments, one or more banks of batteries can be configured to provide electrical power. In some embodiments, the power supply 110 and energy source 119 can be implemented together, as in some all-electric cars.

Many or all of the functions of vehicle 100 can be controlled via computer system 112 that receives inputs from the sensor system 104, peripherals 108, etc., and communicates appropriate control signals to the propulsion system 102, control system 106, peripherals, etc. to effect automatic operation of the vehicle 100 based on its surroundings. Computer system 112 includes at least one processor 113 (which can include at least one microprocessor) that executes instructions 115 stored in a non-transitory computer readable medium, such as the data storage 114. The computer system 112 may also represent a plurality of computing devices that serve to control individual components or subsystems of the vehicle 100 in a distributed fashion.

In some embodiments, data storage 114 contains instructions 115 (e.g., program logic) executable by the processor 113 to execute various functions of vehicle 100, including those described above in connection with FIG. 1. Data storage 114 may contain additional instructions as well, including instructions to transmit data to, receive data from, interact with, and/or control one or more of the propulsion system 102, the sensor system 104, the control system 106, and the peripherals 108.

In addition to the instructions 115, the data storage 114 may store data such as roadway maps, path information, among other information. Such information may be used by vehicle 100 and computer system 112 during operation of the vehicle 100 in the autonomous, semi-autonomous, and/or manual modes to select available roadways to an ultimate destination, interpret information from the sensor system 104, etc.

The vehicle 100, and associated computer system 112, provides information to and/or receives input from, a user of vehicle 100, such as an occupant in a passenger cabin of the vehicle 100. The user interface 116 can accordingly include one or more input/output devices within the set of peripherals 108, such as the wireless communication system 146, the touchscreen 148, the microphone 150, and/or the speaker 152 to allow communication between the computer system 112 and a vehicle occupant.

The computer system 112 controls the operation of the vehicle 100 based on inputs received from various subsystems indicating vehicle and/or environmental conditions (e.g., propulsion system 102, sensor system 104, and/or control system 106), as well as inputs from the user interface 116, indicating user preferences. For example, the computer system 112 can utilize input from the control system 106 to control the steering unit 132 to avoid an obstacle detected by the sensor system 104 and the obstacle avoidance system 144. The computer system 112 can be configured to control many aspects of the vehicle 100 and its subsystems. Generally, however, provisions are made for manually overriding automated controller-driven operation, such as in the event of an emergency, or merely in response to a user-activated override, etc.

The components of vehicle 100 described herein can be configured to work in an interconnected fashion with other components within or outside their respective systems. For example, the camera 130 can capture a plurality of images that represent information about an environment of the vehicle 100 while operating in an autonomous mode. The environment may include other vehicles, traffic lights, traffic signs, road markers, pedestrians, etc. The computer vision system 140 can categorize and/or recognize various aspects in the environment in concert with the sensor fusion algorithm 138, the computer system 112, etc. based on object recognition models pre-stored in data storage 114, and/or by other techniques.

Although the vehicle 100 is described and shown in FIG. 1 as having various components of vehicle 100, e.g., wireless communication system 146, computer system 112, data storage 114, and user interface 116, integrated into the vehicle 100, one or more of these components can optionally be mounted or associated separately from the vehicle 100. For example, data storage 114 can exist, in part or in full, separate from the vehicle 100, such as in a cloud-based server, for example. Thus, one or more of the functional elements of the vehicle 100 can be implemented in the form of device elements located separately or together. The functional device elements that make up vehicle 100 can generally be communicatively coupled together in a wired and/or wireless fashion.

Figure 2:
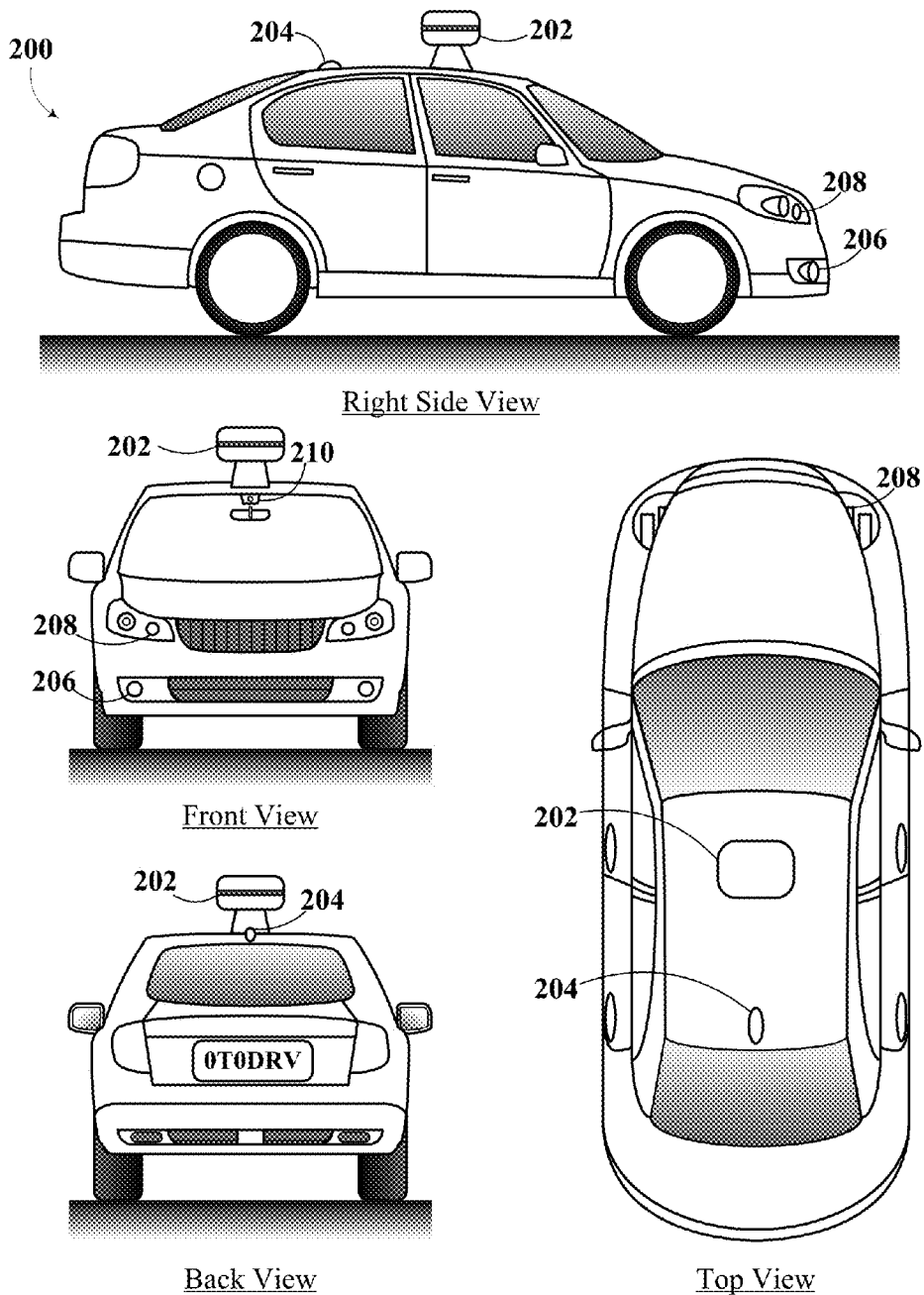
FIG. 2 depicts exterior views of the autonomous vehicle.

FIG. 2 shows an example vehicle 200 that can include some or all of the functions described in connection with vehicle 100 in reference to FIG. 1. Although vehicle 200 is illustrated in FIG. 2 as a four-wheel sedan-type car for illustrative purposes, the present disclosure is not so limited. For instance, the vehicle 200 can represent a truck, a van, a semi-trailer truck, a motorcycle, a golf cart, an off-road vehicle, or a farm vehicle, etc.

The example vehicle 200 includes a sensor unit 202, a wireless communication system 204, a LIDAR unit 206, a laser rangefinder unit 208, and a camera 210. Furthermore, the example vehicle 200 can include any of the components described in connection with vehicle 100 of FIG. 1.

The sensor unit 202 is mounted atop the vehicle 200 and includes one or more sensors configured to detect information about an environment surrounding the vehicle 200, and output indications of the information. For example, sensor unit 202 can include any combination of cameras, RADARs, LIDARs, range finders, and acoustic sensors. The sensor unit 202 can include one or more movable mounts that could be operable to adjust the orientation of one or more sensors in the sensor unit 202. In one embodiment, the movable mount could include a rotating platform that could scan sensors so as to obtain information from each direction around the vehicle 200. In another embodiment, the movable mount of the sensor unit 202 could be moveable in a scanning fashion within a particular range of angles and/or azimuths. The sensor unit 202 could be mounted atop the roof of a car, for instance, however other mounting locations are possible. Additionally, the sensors of sensor unit 202 could be distributed in different locations and need not be collocated in a single location. Some possible sensor types and mounting locations include LIDAR unit 206 and laser rangefinder unit 208. Furthermore, each sensor of sensor unit 202 could be configured to be moved or scanned independently of other sensors of sensor unit 202.

The wireless communication system 204 could be located on a roof of the vehicle 200 as depicted in FIG. 2. Alternatively, the wireless communication system 204 could be located, fully or in part, elsewhere. The wireless communication system 204 may include wireless transmitters and receivers that could be configured to communicate with devices external or internal to the vehicle 200. Specifically, the wireless communication system 204 could include transceivers configured to communicate with other vehicles and/or computing devices, for instance, in a vehicular communication system or a roadway station. Examples of such vehicular communication systems include dedicated short range communications (DSRC), radio frequency identification (RFID), and other proposed communication standards directed towards intelligent transport systems.

The camera 210 can be a photo-sensitive instrument, such as a still camera, a video camera, etc., that is configured to capture a plurality of images of the environment of the vehicle 200. To this end, the camera 210 can be configured to detect visible light, and can additionally or alternatively be configured to detect light from other portions of the spectrum, such as infrared or ultraviolet light. The camera 210 can be a two-dimensional detector, and can optionally have a three-dimensional spatial range of sensitivity. In some embodiments, the camera 210 can include, for example, a range detector configured to generate a two-dimensional image indicating distance from the camera 210 to a number of points in the environment. To this end, the camera 210 may use one or more range detecting techniques.

For example, the camera 210 can provide range information by using a structured light technique in which the vehicle 200 illuminates an object in the environment with a predetermined light pattern, such as a grid or checkerboard pattern and uses the camera 210 to detect a reflection of the predetermined light pattern from environmental surroundings. Based on distortions in the reflected light pattern, the vehicle 200 can determine the distance to the points on the object. The predetermined light pattern may comprise infrared light, or radiation at other suitable wavelengths for such measurements.

The camera 210 can be mounted inside a front windshield of the vehicle 200. Specifically, the camera 210 can be situated to capture images from a forward-looking view with respect to the orientation of the vehicle 200. Other mounting locations and viewing angles of camera 210 can also be used, either inside or outside the vehicle 200.

The camera 210 can have associated optics operable to provide an adjustable field of view. Further, the camera 210 can be mounted to vehicle 200 with a movable mount to vary a pointing angle of the camera 210, such as a via a pan/tilt mechanism.

Figure 3A:
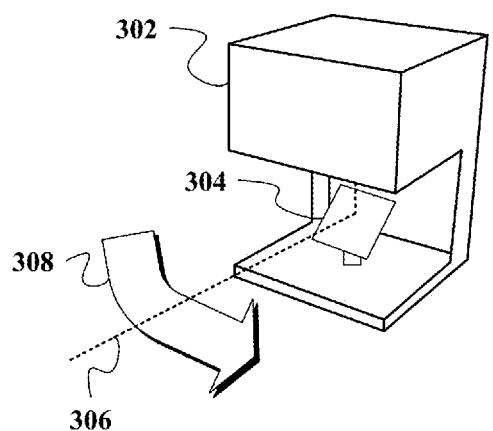
FIG. 3A provides an example depiction of a LIDAR device including beam steering optics.

FIG. 3A provides an example depiction of a light detection and ranging (LIDAR) device 302 including beam steering optics 304. A laser beam 306 is directed to the beam steering optics 304. In the example illustrated in FIG. 3A, the beam steering optics 304 is a rotating angled mirror that directs the initially downward facing laser beam 306 to sweep across a scanning zone. As described herein, the beam steering optics 304, which can generally be implemented as a combination of lenses, mirrors, and/or apertures configured to direct the laser beam to sweep across a scanning zone, are interchangeably described as the rotating angled mirror 304. The rotating angled mirror 304 rotates about an axis substantially parallel, and roughly in line with, the initial downward path of the laser beam 306. The rotating angled mirror 304 rotates in the direction indicated by the reference arrow 308 in FIG. 3A.

Although rangefinder 302 is depicted as having (approximately) a 180 degree range of rotation for the scanning zone of the laser beam 306 via the rotating angled mirror 304, this is for purposes of example and explanation only, as the present disclosure is not so limited. Indeed, as explained above, LIDAR 302 can be configured to have viewing angle (e.g., angular range of available orientations during each sweep), including viewing angles up to and including 360 degrees. Further, although LIDAR 302 is depicted with the single laser beam 306 and a single mirror 304, this is for purposes of example and explanation only, as the present disclosure is not so limited. Indeed, as explained above, LIDAR 302 can include multiple laser beams operating simultaneously or sequentially to provide greater sampling coverage of the surrounding environment. The LIDAR 302 also includes, or works in concert with, additional optical sensors (not shown) configured to detect the reflection of laser beam 306 from features/objects in the surrounding environment with sufficient temporal sensitivity to determine distances to the reflective features. For example, with reference to the vehicle 200 in FIG. 2, such optical sensors can optionally be co-located with the top-mounted sensors 204 on the autonomous vehicle 200.

Figure 3B:
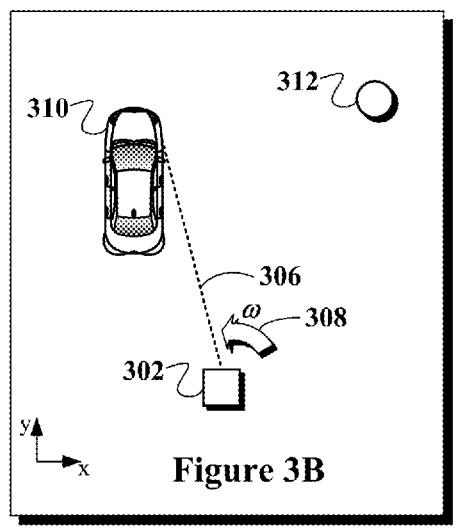
FIG. 3B symbolically illustrates a LIDAR device scanning across an obstacle-filled environmental scene.

FIG. 3B symbolically illustrates the LIDAR device 302 scanning across an obstacle-filled environmental scene. The example vehicular environment depicted in FIG. 3B includes a car 310 and a tree 312. In operation, LIDAR 302 rotates according to motion reference arrow 308 with angular velocity ω. While rotating, the LIDAR 302 regularly (e.g., periodically) emits laser beams, such as the laser beam 306. Reflections from the emitted laser beams by objects in the environment, such as vehicle 310 and tree 312, are then received by suitable sensors. Precisely time-stamping the receipt of the reflected signals allows for associating each reflected signal (if any is received at all) with the most recently emitted laser pulse, and measuring the time delay between emission of the laser pulse and reception of the reflected light. The time delay provides an estimate of the distance to the reflective feature by scaling according to the speed of light in the intervening atmosphere. Combining the distance information for each reflected signal with the orientation of the LIDAR device 302 for the respective pulse emission allows for determining a position of the reflective feature in three-dimensions. For illustrative purposes, the environmental scene in FIG. 3B is described in the two-dimensional x-y plane in connection with a single sweep of the LIDAR device 302 that estimates positions to a series of points located in the x-y plane. However, it is noted that a more complete three-dimensional sampling is provided by either adjusting the beam steering optics 304 to direct the laser beam 306 up or down from the x-y plane on its next sweep of the scene or by providing additional lasers and associated beam steering optics dedicated to sampling point locations in planes above and below the x-y plane shown in FIG. 3B, or combinations of these.

Figure 3C:
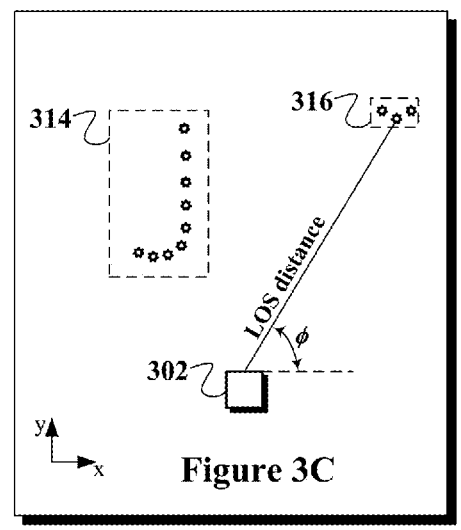
FIG. 3C symbolically illustrates a point cloud corresponding to the obstacle-filled environmental scene of FIG. 3B.

FIG. 3C symbolically illustrates a point cloud corresponding to the obstacle-filled environmental scene of FIG. 3B. Spatial-point data (represented by stars) are shown from a ground-plane (or aerial) perspective. Even though the individual points are not equally spatially distributed throughout the sampled environment, adjacent sampled points are roughly equally angularly spaced with respect to the LIDAR device 302. Car spatial data 314 correspond to measured points on the surface of the car 310 with a line of sight to the LIDAR device 302. Similarly, tree spatial data 316 correspond to measured points on the surface of the tree 312 visible from the LIDAR device 302.

Each point in the example point cloud illustrated symbolically in FIG. 3C can be referenced by an azimuth angle φ (e.g. orientation of the LIDAR device 302 while emitting the pulse corresponding to the point, which is determined by the orientation of the rotating angled mirror 304) and a line-of-sight (LOS) distance (e.g., the distance indicated by the time delay between pulse emission and reflected light reception). For pulses that do not result in a returning reflected signal, the distance in the 3-D point map can optionally be set to the maximum distance sensitivity of the LIDAR device 302. The maximum distance sensitivity can be determined according to the maximum time delay the associated optical sensors wait for a return reflected signal following each pulse emission, which can itself be set according to the anticipated signal strength of a reflected signal at a particular distance given ambient lighting conditions, intensity of the emitted pulse, predicted reflectivity of environmental features, etc. In some examples, the maximum distance can be approximately 60 meters, 80 meters, 100 meters, or 150 meters, but other examples are possible for particular configurations of the LIDAR device 302 and associated optical sensors.

In some embodiments, the sensor fusion algorithm 138, computer vision system 140, and/or computer system 112, can interpret the car spatial data 314 alone and/or in combination with additional sensor-indicated point information and/or memory-based pattern-matching point clouds and/or baseline maps of the environment to categorize or identify the group of points 314 as corresponding to the car 310. Similarly, the tree spatial data 316 can identified as corresponding to the tree 310 in accordance with a suitable object-detection technique. As described further herein, some embodiments of the present disclosure provide for identifying a region of the point cloud for study with enhanced resolution scanning technique on the basis of the already-sampled spatial-points.

Further, as noted above, each spatial point can be associated with a respective laser from a set of lasers and a respective timestamp. That is, in an embodiment where the LIDAR 302 includes multiple lasers, each respective received spatial point can be associated with the particular laser that was detected in accordance with the respective received spatial point. Additionally, each respective spatial point can be associated with a respective timestamp (e.g., a time at which laser was emitted or received). In this way, the received spatial points may be organized, identified, or otherwise ordered on a spatial (laser identification) and/or temporal (timestamp) basis. Such an ordering may assist or improve an analysis of the spatial-point data by allowing for organizing the spatial-point data into a meaningful order.

Figure 4A:
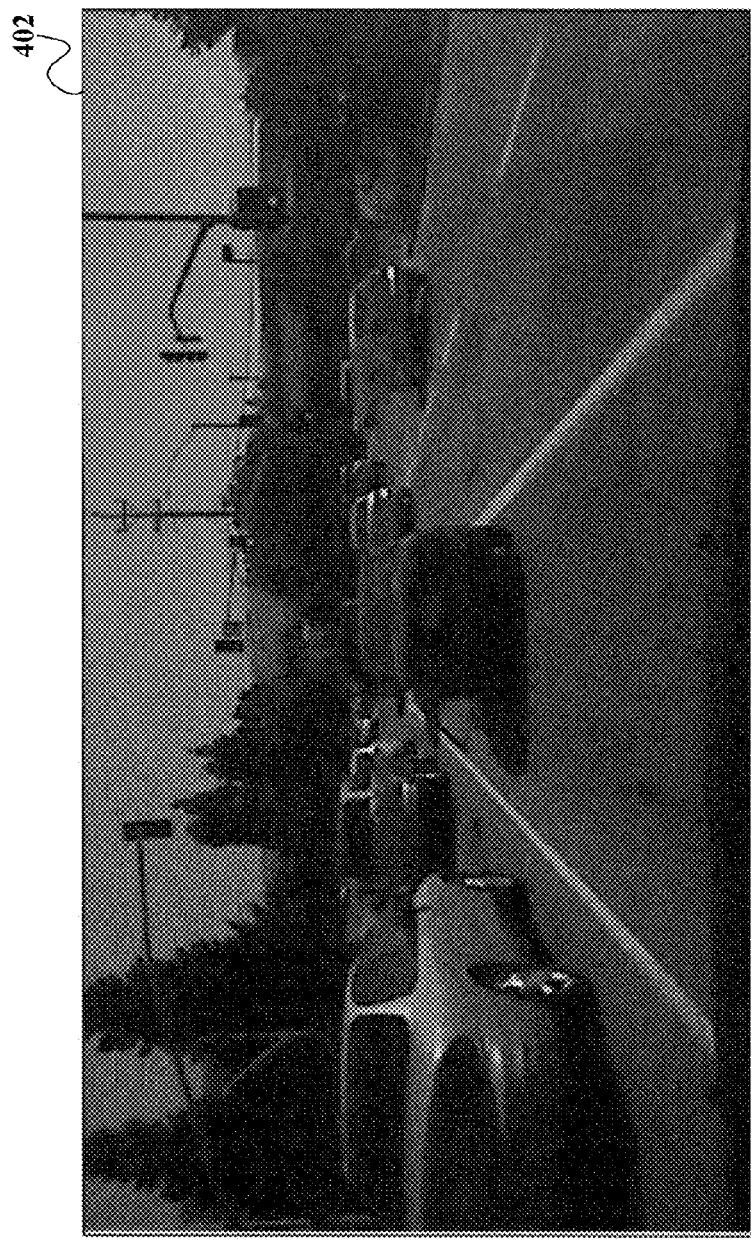
FIG. 4A is an image of an example roadway approaching an intersection.
Figure 4B:
FIG. 4B is a rendering of a LIDAR-indicated point cloud corresponding to the scene pictured in FIG. 4A.
Figure 4C:
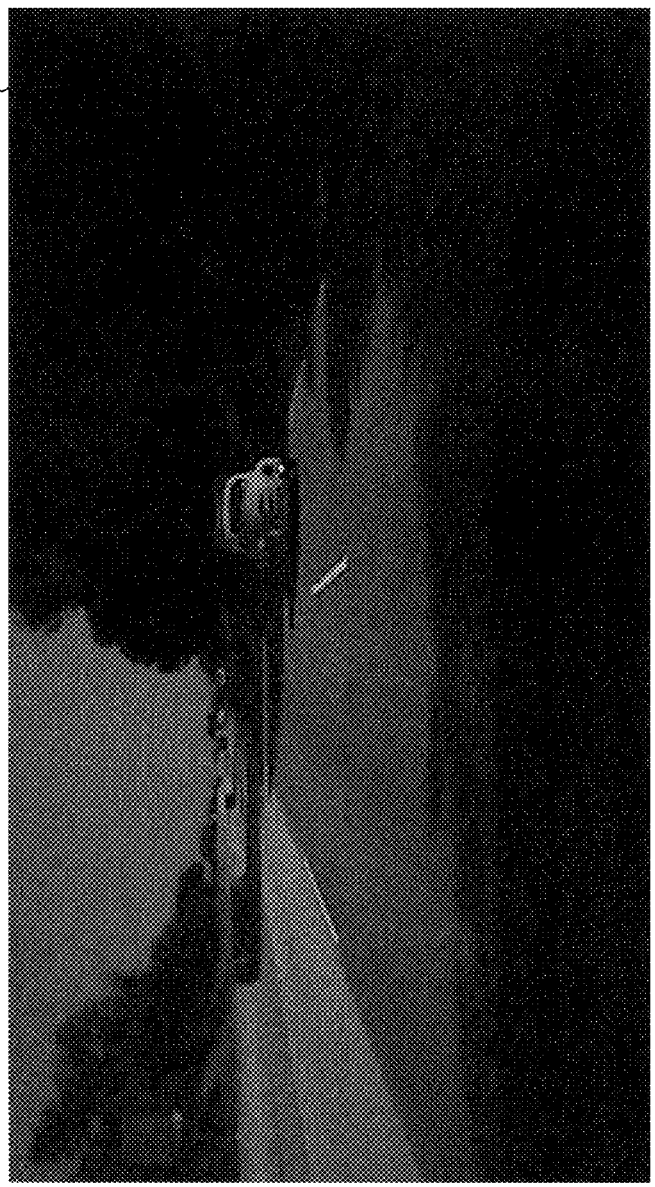
FIG. 4C is an image of another example roadway.
Figure 4D:
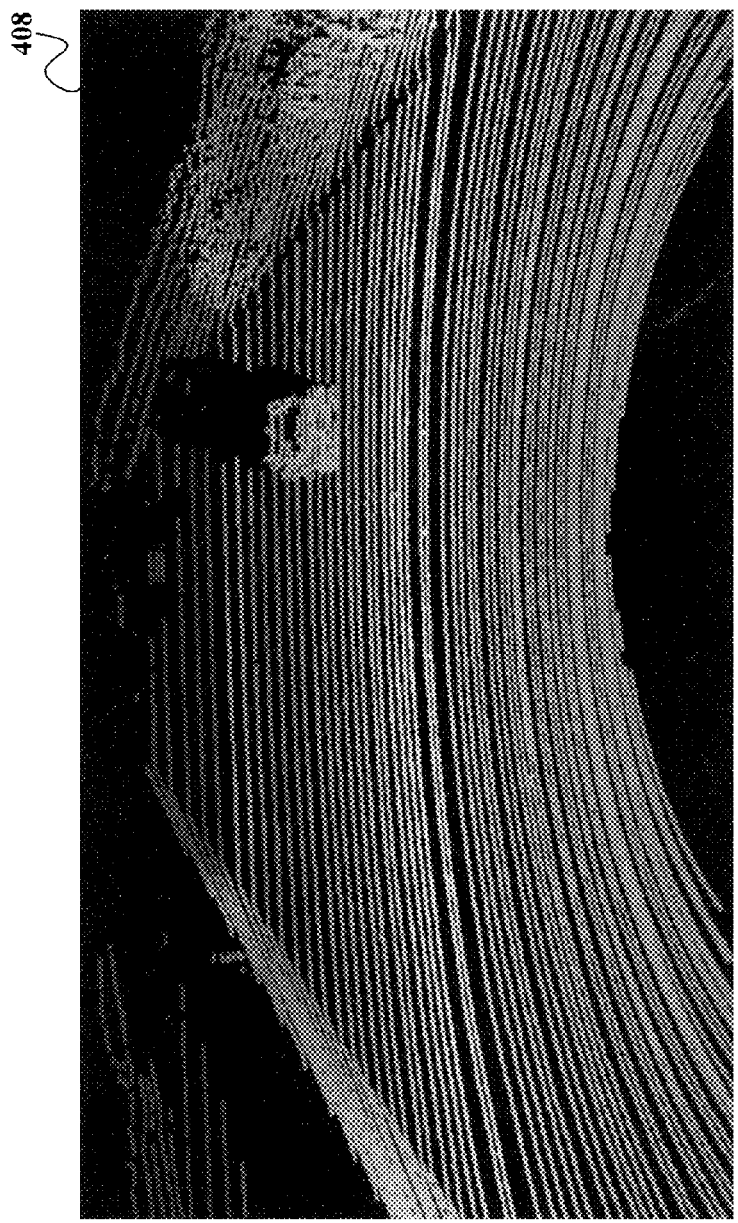
FIG. 4D is a rendering of a LIDAR-indicated point cloud corresponding to the scene pictured in FIG. 4C.

FIG. 4A is a raw camera image of an example roadway scene 402 approaching an intersection. FIG. 4B is a rendering of a LIDAR-indicated point cloud 404 corresponding to the scene 402 pictured in FIG. 4A. FIG. 4C is a raw camera image of another example roadway scene 406. FIG. 4D is a rendering of a LIDAR-indicated point cloud 408 corresponding to the scene 406 pictured in FIG. 4C.

With reference to the vehicle 200 of FIG. 2, the camera images 402, 406 of FIGS. 4A and 4C can be captured by the camera 210 of the vehicle 200, and the corresponding point cloud maps 404, 408 of FIGS. 4B and 4D can be captured by the LIDAR sensor 206. As shown in the examples of FIGS. 4B and 4D, a laser point cloud image may substantially or approximately correspond to a raw camera image captured by a camera. Moreover, FIGS. 4B and 4D show that LIDAR-indicated point cloud maps for the distinct environmental scenes 402, 406 (i.e., the images in FIGS. 4A and 4C) result in distinct point maps 404, 408 which correspond to their respective scenes. For clarity it is noted that each "line" depicted in FIGS. 4B and 4D generally corresponds to a series of spatial points collected by a particular, single, laser of LIDAR 206.

For purposes of context, example, and explanation, an overview of general approaches to object detection is provided below in connection with an example LIDAR device. As noted above, example vehicle 100 includes a LIDAR device 128. LIDAR 128 actively captures laser point cloud images using one or more lasers. The laser point cloud includes many points for each pulse emitted from the LIDAR device 128: reflected signals indicate actual locations of reflective objects, whereas failing to receive reflected signals indicate an absence of sufficiently reflective objects within a particular distance along the line of sight of the laser. Depending on factors including the laser pulse rate, the scene refresh rate, the total solid angle sampled by each LIDAR device (or just the total solid angle of the scene, where only one LIDAR device is used), the number of sample points in each point cloud can be determined. Some embodiments can provide point clouds with as many as 50,000 laser-indicated points, 80,000 laser-indicated points, 100,000 laser-indicated points, etc. Generally, the number of laser-indicated points in each point cloud is a tradeoff between angular resolution on the one hand, and refresh rate on the other hand. The LIDAR device is driven to provide an angular resolution at a sufficiently high refresh rate to be relevant to real time navigational decisions for an autonomous vehicle. Thus, the LIDAR 128 can be configured to capture one or more laser point clouds of the scanning zone at predetermined time intervals, such as 100 milliseconds (to achieve a refresh rate of 10 frames per second), 33 milliseconds (to achieve a refresh rate of 30 frames per second), 1 millisecond, 1 second, etc.

Data storage 114 of computer system 112 of vehicle 100 can store object-detector software, code, or other program instructions. Such object-detector software can include, or be part of, one or more of the control systems 106 described above, including the sensor fusion algorithm 138, computer vision system 140, and/or obstacle avoidance system 144. The object detector may be any configuration of software and/or hardware configured to perceive features in the environmental scene by categorizing and/or identifying objects based on the laser point clouds captured by the LIDAR 128 and/or based on one or more of the sensors in sensor system 104. As a laser point cloud is captured via LIDAR 128, data indicative of the captured point cloud is communicated to the object detector, which analyzes the data to determine whether there is an object present in the laser point cloud. Objects indicated by the point cloud may be, for example, a vehicle, a pedestrian, a road sign, a traffic light, a traffic cone, etc.

To determine whether an object is present in a laser point cloud image, the object detector software and/or module can associate arrangements of laser-indicated points with patterns matching objects, environmental features, and/or categories of objects or features. The object detector can be pre-loaded (or dynamically instructed) to associate arrangements according to one or more parameters corresponding to physical objects/features in the environment surrounding the vehicle 100. For example, the object detector can be pre-loaded with information indicating a typical height of a pedestrian, a length of a typical automobile, confidence thresholds for classifying suspected objects, etc.

When the object detector identifies an object in point cloud, the object detector can define a bounding box encompassing the object that. For example, the bounding box can correspond to a predicted exterior surface of the point cloud indicated object. Of course, the bounding "box" can generally take the form of a multi-sided closed shape defining the predicted outer boundaries of the object.

For each captured point cloud, positions of perceived objects and their corresponding boundary definitions are associated with a frame number or frame time. Thus, similarly shaped objects appearing in roughly similar locations in successive scans of the scene can be associated with one another to track objects in time. For perceived objects appearing in multiple point cloud frames (e.g., complete scans of the scanning zone), the object can be associated, for each frame on which the object appears, with a distinct bounding shape defining the dimensional extent of the perceived object.

Perceived objects can be tracked as the vehicle 100 travels through its surrounding environment and/or as objects move with respect to the vehicle so as to pass through the scanning zone of the LIDAR 128. Combining two or more successively captured point clouds can thereby allow for determining translation information for detected objects. Future position predictions can be made for objects with characterized motion profiles, such as by observing acceleration and/or velocity of objects such as cars moving along the roadway with the vehicle 100 to predict the location of the object during a subsequent scan. In some embodiments, objects moving through the air are assumed to move along a trajectory influenced by the force of gravity.

To assist in providing object recognition, the vehicle 100 can also be in communication with an object-identification server (e.g., via the wireless communication system 146). The object-identification server can verify and/or classify objects detected by vehicle 100 using the object detector. Moreover, the object-identification server can facilitate optimization of one or more of the parameters used by the object detector to detect objects in the captured laser point cloud based on accumulated data from other similar systems, local conditions. In one embodiment, vehicle 100 can communicate the object boundaries, and their corresponding object parameters, to the object identification server for verification that the perceived objects are correctly identified, such as indicated by an evaluation for statistical likelihood of correct identification.

FIGS. 5A-5C illustrate exemplary non-solid reflective features that can be detected by a LIDAR. As described above, for an autonomous vehicle configured to automatically adjust navigational decisions so as to avoid obstacles perceived in the path of the vehicle, it is desirable to differentiate between non-solid features that do not present obstacles and solid features that do. As described herein, a hyperspectral sensor can be employed to spectrally characterize suspect reflective features, and the feature can be characterized as solid or non-solid by identifying the material in the feature based on the spectral signature of the feature.

FIG. 5A is a side view of a car 500 driving on wet pavement so as to generate a distribution of water (e.g., the spray patterns 522, 524) trailing each wheel (e.g., the wheels 512, 514). FIG. 5B is a back view of the car 500 driving on wet pavement so as to generate a distribution of water (e.g., the spray patterns 526, 524) trailing each wheel (not visible). On wet pavement, treads on the tires of the wheels 512, 514 displace water away from the footprint of the tires to allow the raised portions of the tires to achieve traction with the pavement. Generally, standing water is displaced to either side of the tires and some remains in the grooves of the tire treads. As the tire continues to rotate away from the pavement, water in the grooves of the tire treads initially travels with the rotation and is projected tangentially away from the edge of the rotating tire. As the individual droplets of water are directed tangentially up and away from the bottom of the rotating tire, a spray pattern of water droplets results from the distribution of water droplets. While a turbulent process, the spray pattern can be considered a grouping of water droplets each generally traveling trajectories originating substantially tangential to the edge of the rotating tire, and falling under the force of gravity and atmospheric drag to return to the pavement surface. In some embodiments, a portion of the water spray can be influenced by a surface of the car 500, such as a mud flap, bumper, rocker panel, etc. The combination of many such droplets provides characteristic distributions of water spray that can resemble elongated lobes trailing each tire. Of course, depending on the tread pattern of the tires, the depth of the standing water, the shape of the body of the car 500, the speed of the car 500, etc., the distribution of water droplets can have other shapes and may be non-uniform.

For example, while traveling on wet surface, water in the treads of the tire on the front wheel 512 is conveyed tangentially away from the front wheel 512 and falls back to the pavement to form the spray pattern 522 trailing the front wheel 512. Similarly, water in the treads of the tire on the wheel 514 is conveyed tangentially away from the wheel 514 and falls back to the pavement to form the spray pattern 524 trailing the wheel 514. Another spray pattern 526 trails the second rear wheel.

FIG. 5C is a back view of the car 500 emitting a plume 532 of exhaust gas from a rear tail pipe 530. The tail pipe 530 discharges exhaust gas from a combustion chamber inside an engine of the car 500 that converts chemical fuel energy to mechanical energy to power the car 500. The exhaust gas is generally at a higher temperature than ambient air, and so it disperses from the tail pipe 530 in a plume pattern 532 characterized by the tendency of the heated gas to rise in the ambient air and also disperse by convection according to the direction of prevailing winds. Furthermore, while the car 500 is in motion, the exhaust plume 532 generally trails behind the car 500. The exhaust plume 532 is formed by a combination of heated gases (e.g., nitrogen, oxygen, water vapor, carbon dioxide, carbon monoxide, etc.) and particulates (e.g., hydrocarbons, soot, oxides, etc.) that disperse to the ambient air from the tail pipe 530. Upon emission, the gases thermally regulate with the surrounding air, and the constituents of the exhaust gas diffuse to the surrounding air such that the exhaust becomes substantially indistinguishable. The characteristic exhaust plume 532 is therefore continuously regenerated by exhausted heated gases and particulates emitted from the tail pipe 530 so as to maintain the characteristic plume pattern 532.

To a LIDAR device, which detects and locates optically reflective features, the spray patterns 522-526 resemble a reflective object, because light pulses are reflected from the individual water droplets dispersed throughout the spray pattern. From the rear, the resulting spray patterns 524, 526 can be interpreted by a LIDAR as a pair of extended lobes extending behind the car 500. Similarly, the exhaust plume 532 resembles a reflective cloud, because light pulses are reflected from the particulates, such as water droplets, particulates due to incomplete exhaustion reactions, etc, dispersed throughout the exhaust cloud 532. The temperature of the ambient air can influence the perception of the exhaust plume 532. For example, water droplets formed by condensation within the exhausted gases are formed more quickly (i.e., closer to the tail pipe 530) when the ambient temperature is cold than when the ambient temperature is hot and condensation occurs more slowly (i.e., further from the tail pipe 530). Thus, the exhaust plume 532 can be more readily apparent on cold days, because water droplets are formed in greater numbers closer to the tail pipe 530 and the spatial density of reflective water droplets near the tail pipe 530 is increased. Similarly, the exhaust plume 532 can be more readily apparent immediately after a car is started while it is still warming up, because the exhaust gases emitted from the tail pipe 530 are relatively colder than after the exhaust gases warm to their normal operating temperature, and as a result water droplets form more readily closer to the tail pipe 530.

Figure 6A:
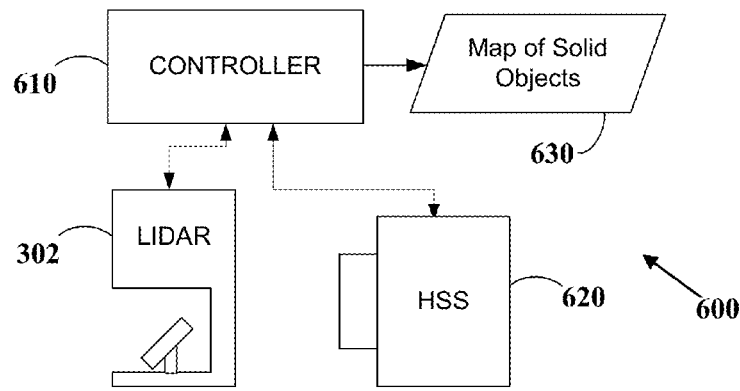
FIG. 6A is a block diagram of a system for employing a hyperspectral sensor to determine whether a LIDAR indicated reflective feature includes a solid material.

FIG. 6A is a block diagram of a system 600 for employing a hyperspectral sensor 620 to determine whether a LIDAR indicated reflective feature includes a solid material. The system 600 includes both the LIDAR device 302 and a hyperspectral sensor 620 configured to detect and locate objects in a scanning zone mapped by the system 600. In some embodiments, the hyperspectral sensor 620 can be mounted to the vehicle 200, such as in the sensor unit 202. The LIDAR device 302 can also be mounted to the vehicle 200, such as in the LIDAR unit 206 and/or sensor unit 202. The hyperspectral sensor 620 can detect spectral content of received radiation in a pixelated pattern to spectrally characterize the surrounding environment in a spatially selected ("pixelated") manner. For example, the hyperspectral sensor 620 can include both imaging optics and a spectral selectivity module. The imaging optics can be one or more lenses, mirrors, shutters, and/or apertures arranged to focus received radiation on an imaging plane that includes a photo sensitive detector, such as a charge coupled device array, or a similar detector for generating electrical signals related to an intensity pattern in the imaging plane. The spectral selectivity module can include a grating for redirecting incoming radiation in a wavelength-dependent manner (e.g., incoming radiation is deflected by an angle that is dependent on wavelength). A photo sensitive detector array can then provide information on the spectral distribution (i.e., wavelength distribution) of the deflected radiation, with distinct regions of the detector array corresponding to intensity in distinct spectral bands. Additionally or alternatively, the spectral selectivity module can include one or more filters configured to selectively pass ("transmit") received radiation according to its wavelength.

The spectral content of received radiation can be determined by repeatedly imaging the same scene, with each image taken with a filter for a distinct spectral band. Accumulating a series of such images can characterize the spectral content of an imaged scene (e.g., the first image can indicate the intensity at a first wavelength band, the next image at a second wavelength band, etc.). Additionally or alternatively, hyperspectral sensor 620 can generate a spectrally characterized image by scanning across a scene while spectrally characterizing a portion of the scene via a grating. Moreover, one or more beam splitting mirrors and/or holographic prisms can be included in the hyperspectral sensor 620 to image a scene through different filters simultaneously. For example, radiation received through a primary aperture can be optically divided and passed through two different filters to allow for simultaneously imaging a scene with spectral sensitivity in the bands of the two filters. Similarly, beam splitting mirrors and/or holographic prims can be included to allow for simultaneously analyzing two different regions of an imaged scene. The hyperspectral sensor 620 outputs a pixelated image of a scene where each pixel includes intensity values for multiple spectral bands. Combining the intensity values provides a spectrum of the radiation received at the hyperspectral sensor 620 on a pixel-by-pixel basis. As a result, the hyperspectral sensor 620 allows for distinguishing the spectral distribution of received light from different spatial regions of an imaged scene (i.e., different pixels).

The spectral range of sensitivity (e.g., the range of wavelengths of radiation detectable via the hyperspectral sensor 620) can include one or more of ultraviolet radiation, visible radiation, near infrared radiation, infrared radiation, etc. Moreover, in some embodiments multiple hyperspectral sensors can be employed where each has a distinct range of spectral sensitivity, such as where one detects ultraviolet and visible radiation and another detects infrared radiation. In some embodiments, the hyperspectral sensor 620 is sensitive to a substantially continuous spectral range including at least a part of the near infrared spectrum (e.g., approximately 900 nm to approximately 1700 nm).

A controller 610 is in communication with both the LIDAR device 302 and the hyperspectral sensor 620 to send and receive data. The controller 610 can, for example, send command and control instructions to the LIDAR device 302 and hyperspectral sensor 620 to cause one or both devices to carry out measurements in a specified region and/or at a specified time. The controller 610 can also, for example, receive data indicative of three dimensional locations of reflective points in the surrounding environment (e.g., from the LIDAR device 302) and/or data indicative of spectral characteristics of the surrounding environment (e.g., from the hyperspectral sensor 620).

Different materials in the environment surrounding the system 600 reflect, emit, and/or transmit radiation with different spectral signatures. The spectral content of the environmental scene thus allows for identifying materials in the environmental scene according to spectral characteristics. For example, materials can be characterized according to atomic and/or molecular absorption and/or emission characteristics. In some embodiments, reduction in radiation at a spectral band relative to, e.g., the solar spectrum, indicates an atomic and/or molecular structure susceptible to selectively absorbing radiation in the spectral band. In some embodiments, a fluorescent material can be indicated by relative less radiation at one spectral band and relatively more radiation at another spectral band.

In the system 600, the controller 610 operates the LIDAR device 302 and the hyperspectral sensor 620 to spectrally characterize reflective features indicated by the LIDAR device 302. The controller 610 interprets the spectrally characterized reflective features to associate the reflective features with either solid materials or not solid materials and output a map of solid objects 630 in the environment surrounding the system 600.

Figure 6B:
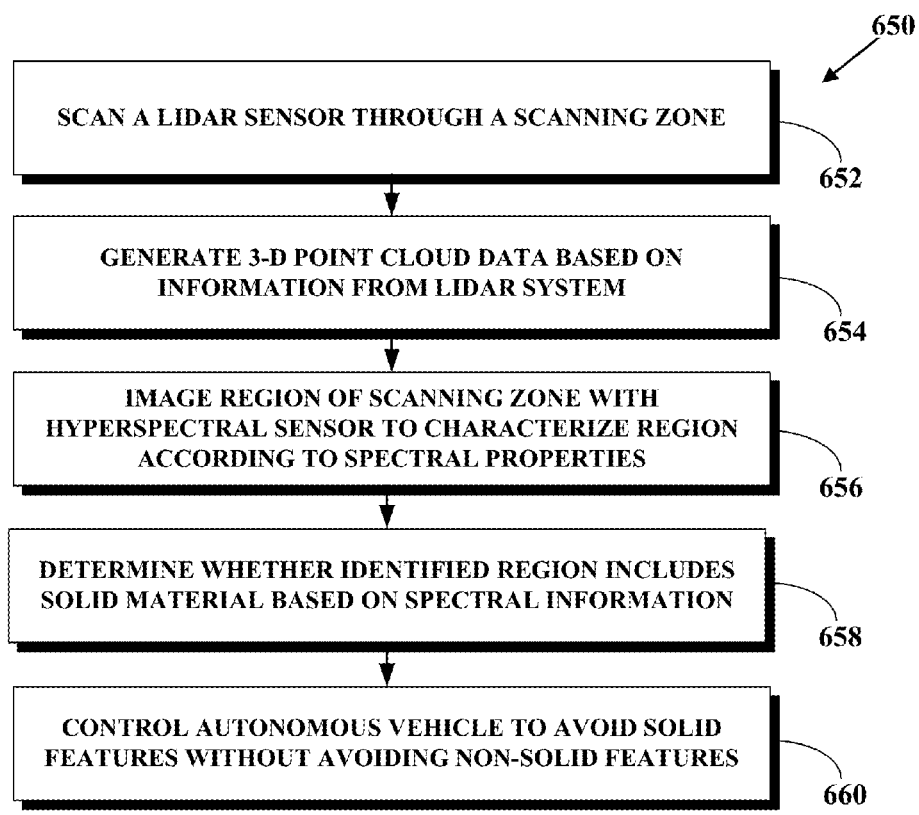
FIG. 6B is a flowchart of a process for employing a hyperspectral sensor to determine whether a LIDAR indicated reflective feature includes a solid material.

FIG. 6B is a flowchart 650 of a process for employing the hyperspectral sensor 620 to determine whether a LIDAR indicated reflective feature includes a solid material. The LIDAR device 302 is scanned through a scanning zone (652). The controller 610 generates a three-dimensional (3-D) point cloud based on information from the LIDAR device 302 (654). For example, the LIDAR device 302 and/or associated optical detectors can output information indicative of time delays for reflected light signals corresponding to emitted light pulses to reach the optical detectors. The LIDAR device 302 can also provide information indicative of the orientation of the LIDAR device 302 for each pulse emission such that a direction and distance is associated with each returned reflected light signal to generate the 3-D point cloud. A region of the scanning zone is imaged with the hyperspectral sensor 620 to spectrally characterize the region (656). In some embodiments, all LIDAR-indicated objects in the scanning zone are imaged via the hyperspectral sensor 620. In some embodiments, the controller 610, sensor fusion algorithm 138, and/or computer visions system 140, etc. analyze the LIDAR indicated 3-D point cloud and identify a region to analyze with the hyperspectral sensor 620. The spectral information from the hyperspectral sensor 620 is analyzed to determine whether a solid material is included in the region (658). An autonomous vehicle associated with the LIDAR 302 and hyperspectral sensor 620 is controlled to avoid solid features without avoiding non-solid features (660). Solid features to avoid can be, for example, LIDAR-indicated reflective features with corresponding spectral information associated with a solid material. Non-solid features to not avoid (i.e., to ignore) can be, for example, LIDAR-indicated reflective features with corresponding spectral information associated with a non-solid material. Example processes for determining whether a reflective feature includes a solid material or a non-solid material are described in connection with FIGS. 8A and 8B herein.

Figure 7:
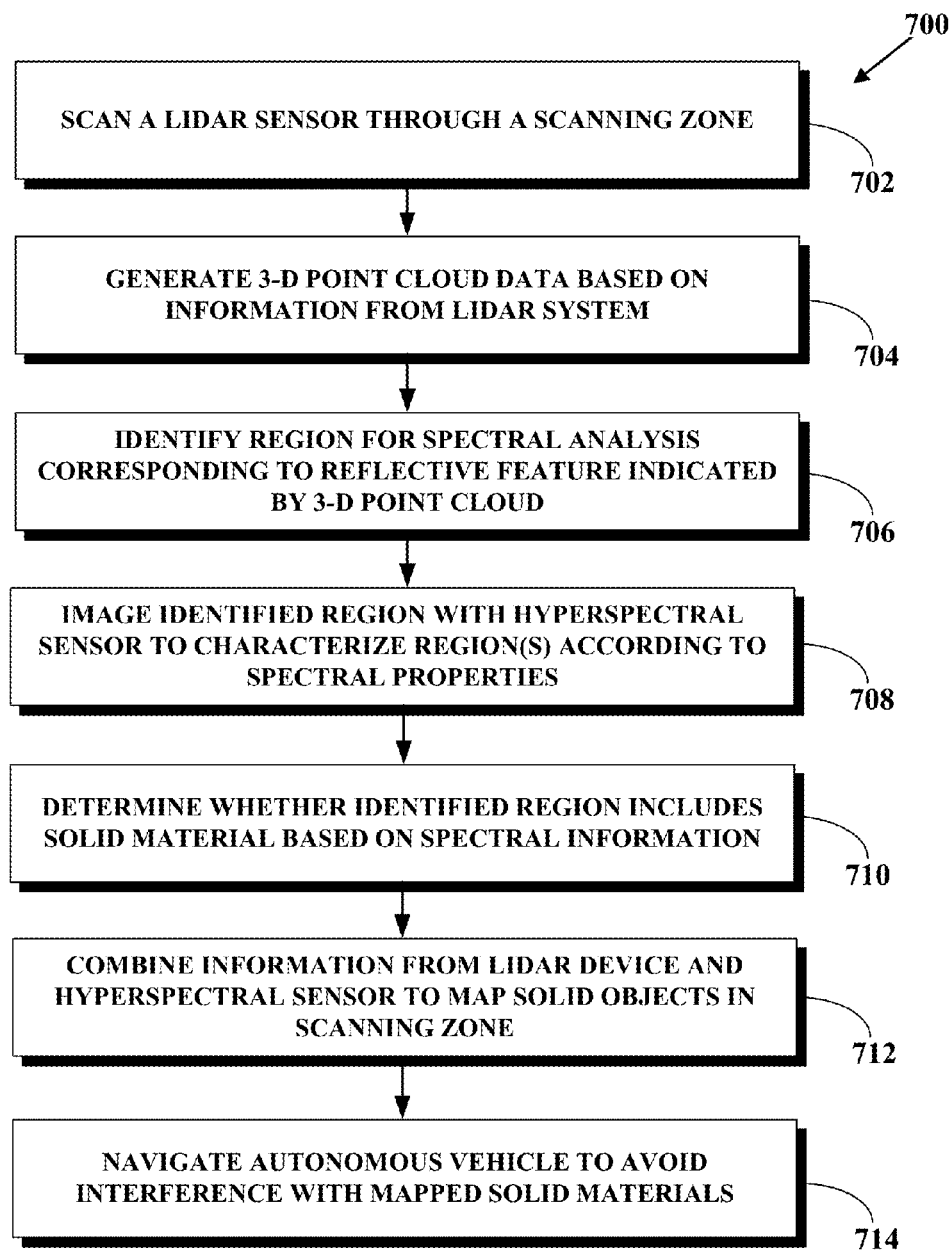
FIG. 7 is a flowchart of a process for navigating an autonomous vehicle according to environmental feedback information from both a LIDAR device and hyperspectral sensor.

FIG. 7 is a flowchart 700 of a process for navigating an autonomous vehicle according to real time environmental feedback information from both the LIDAR device 302 and the hyperspectral sensor 620. The LIDAR device 302 is scanned through a scanning zone surrounding the vehicle (702). Information from reflected light signals provided by the LIDAR device 302 and/or associated optical detectors is analyzed to generate a 3-D point cloud of positions of reflective features in the scanning zone (704). The 3-D point cloud is analyzed via the controller 610, the sensor fusion algorithm 138, the computer vision system 140, and/or the object detection module described above, etc. to identify regions of the scanning zone for spectral analysis (706). The region identified for spectral analysis (706) can be a region including a LIDAR-indicated reflective feature/object. In some embodiments, reflective features in the scanning zone that resemble optically reflective non-solid features are identified for spectral analysis (706). For example, regions can be identified that include reflective features resembling water spray patterns, such as the spray patterns 522, 524 shown in FIGS. 5A-5B, and/or reflective features resembling gaseous exhaust plumes, such as exhaust plume 532 shown in FIG. 5C. In such an example, the spectral characterization by the hyperspectral sensor 620 provides verification of suspected non-solid objects.

The identified region is identified with the hyperspectral sensor 620 to characterize the region according to its spectral properties (708). The spectral information is used to determine whether the region includes a solid material (710). For example, an imaged region can be determined to include water spray when the region is spectrally characterized by absorption in spectral bands associated with water vapor and/or atomized water droplets. In some embodiments, the imaged region can be determined to include exhaust gas when the region is spectrally characterized by absorption in spectral bands associated with carbon monoxide, water vapor or droplets, particulates associated with incomplete combustion reactions, and/or another gas disproportionately present in exhaust gasses relative to atmospheric concentrations. The present disclosure can be employed to spectrally characterize exhaust plumes with a different chemical constituents, such as white exhaust plumes caused by water droplets forming in the plume; blue exhaust plumes caused by particulates in the exhaust due to oil in the combustion chamber; black or gray exhaust plumes caused by particulates in the exhaust due to incomplete combustion reactions. In some embodiments, spectral signatures can be associated with one or more other encountered environmental materials, such as concrete, asphalt, granite, steel, aluminum, glass, wood, vegetation such as leaves, foliage, grass, surfaces of trees, etc. The 3-D point cloud information from the LIDAR device can be combined with the indications of whether reflective features are solid or not solid to map solid objects in the scanning zone (712). For examples, where reflective features are determined to be water spray, an exhaust plume, and/or another fluid, non-solid material, the 3-D point cloud generated according to information from the LIDAR device 302 can be modified to remove the non-solid objects from the point cloud, leaving only solid objects.

The autonomous vehicle is navigated to avoid interference with objects in the map of solid objects 630 (714). In some embodiments, non-solid LIDAR-indicated features, such as water spray patterns and/or exhaust plumes are substantially ignored by the navigation control systems operating the autonomous vehicle. For example, the object avoidance system 144 and/or navigation/pathing system 142 can be provided with the map of solid objects 630 to automatically determine a path for the autonomous vehicle that avoids solid objects without avoiding splashes of water or exhaust plumes even if optically opaque. Thus, in some embodiments of the present disclosure, information from both the LIDAR device 302 and the hyperspectral sensor 620 is combined generate the map of solid objects 630.

In some examples, the map of solid objects 630 is a map of reflective features indicated by the LIDAR device 302 that omits any features spectrally determined to not include solid materials. The combination of information from the two sensors to create the map of solid objects 630 can be carried out by, for example, the controller 610 implemented as hardware and/or software modules including one or more of the computer system 112, the sensor fusion algorithm 138, the computer visions system 140, etc of the autonomous vehicle 100. The controller can analyze positions of the solid objects in the map of solid objects 630 in relation to a current path of the vehicle 100 to identify obstacles and/or interference with the vehicle 100 indicated by the map of solid objects 100. The controller 610, which can include hardware and/or software implemented modules including the navigation/pathing system 142, the obstacle avoidance system 144, etc. can determine a modified path for the autonomous vehicle 100. For example, the controller 610 can determine a path that minimizes interference with solid objects in the map of solid objects 630, or that maximizes passenger safety during an unavoidable collision/interference with an obstacle by the vehicle 100. The controller 610 can then control the autonomous vehicle 100 to navigate along the modified path. Thus, in some embodiments, the map of solid objects 630 is generated and/or updated repeatedly and used as feedback to inform real time navigation determinations made by an autonomous vehicle operating substantially without human control. As a result, some embodiments of the present disclosure provide for the map of solid objects 630 to be generated and/or updated at a refresh rate that is relevant to real time navigational determinations by an autonomous vehicle.

Figure 8A:
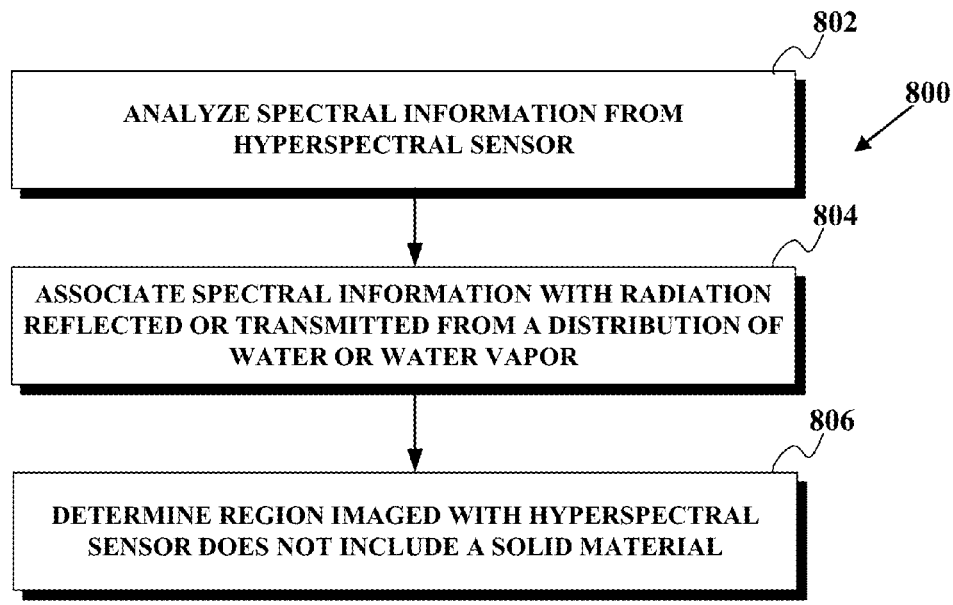
FIG. 8A is a flowchart of a process for determining that a region imaged with a hyperspectral sensor does not include a solid material.

FIG. 8A is a flowchart 800 of a process for determining that a region imaged with the hyperspectral sensor 630 does not include a solid material. Spectral information from an image captured by the hyperspectral sensor 630 is analyzed (e.g., via the controller 610, sensor fusion algorithm 138, etc.) (802). Spectral content in a region of the image is associated with radiation reflected or transmitted from a distribution of water droplets and/or water vapor (804). For example, the spectral profile of the region imaged by the hyperspectral sensor 630 can indicate absorption and/or emission in spectral bands corresponding to water droplets and/or water vapor. The spectral profile can also include indications of absorption and/or emission in spectral bands corresponding to particulates found in exhaust gases, vegetation, foliage, etc. the spectral profile can include a spectral range including at least a portion of the near infrared spectrum, e.g., the range from about 900 nm to about 1700 nm. Portions of the imaged region associated with the spectral profile for water are determined to not include solid material (806). The map of solid objects 630 can then reflect that the regions characterized as water do not include a solid material.

Figure 8B:
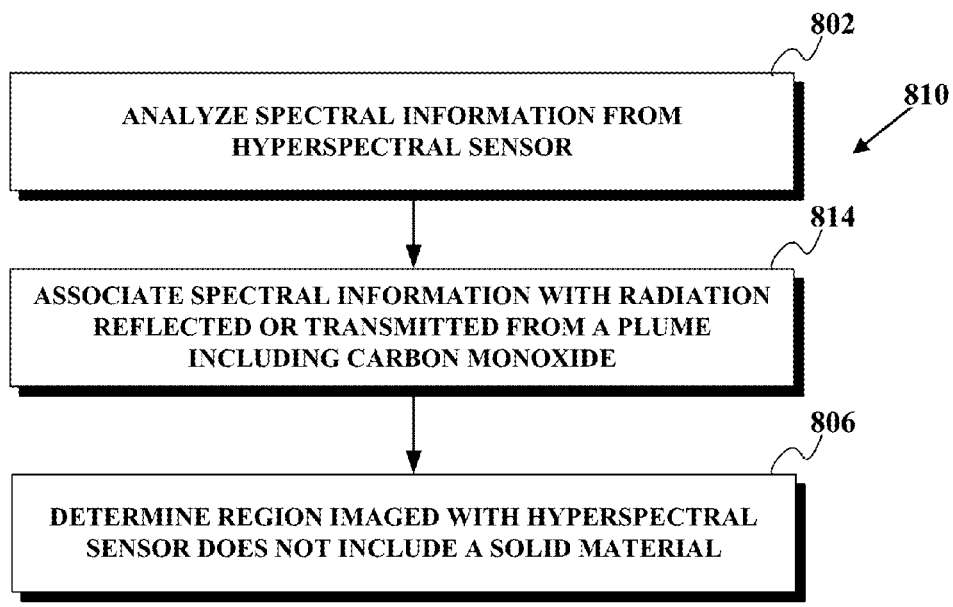
FIG. 8B is a flowchart of another process for determining that a region imaged with a hyperspectral sensor does not include a solid material.

FIG. 8B is a flowchart 810 of another process for determining that a region imaged with the hyperspectral sensor 630 does not include a solid material. Similar to the process discussed in connection with FIG. 8A, spectral information from an image captured by the hyperspectral sensor 630 is analyzed (802). Spectral content in a region of the image is associated with radiation reflected or transmitted from a distribution of gas including carbon monoxide (814). For example, the spectral profile of a region imaged by the hyperspectral sensor 630 can indicate absorption and/or emission in spectral bands corresponding to disproportionate concentrations of carbon monoxide or water. Portions of the imaged region associated with the spectral profile for exhaust gas are determined to not include solid material (806). The map of solid objects 630 can then reflect that the regions characterized as exhaust gas do not include a solid material.

FIGS. 8A and 8B are provided for exemplary purposes only to illustrate the function of distinguishing solid objects from non-solid objects according to spectral characteristics indicated by a hyperspectral sensor. Other examples include determining that regions with spectral profiles indicating absorption and/or emission in spectral bands corresponding to leaves, other foliage, particles of blowing sand or dirt, etc. do not include solid materials. Moreover, some embodiments of the present disclosure include utilizing the ability to distinguish solid materials from non-solid materials to make real time navigation decisions for an autonomous vehicle. Such an autonomous vehicle can thereby operate to avoid collisions and/or interference with solid objects, such as indicated by the LIDAR device 302, the computer vision system 140, etc., while safely ignoring reflective features that do not require comparable navigational adjustments, such as water spray patterns, exhaust plumes, dust clouds, fog, etc.

FIGS. 6B, 7, and 8A-8B present flowcharts describing processes employed separately or in combination in some embodiments of the present disclosure. The methods and processes described herein are generally described by way of example as being carried out by an autonomous vehicle, such as the autonomous vehicles 100, 200 described above in connection with FIGS. 1 and 2. For example, the processes described herein can be carried out by a LIDAR sensor 128 and associated optical sensors (e.g., the sensors 202 on vehicle 200) mounted to an autonomous vehicle (e.g., the vehicle 200) in communication with a computer system 112, sensor fusion algorithm module 138, and/or computer vision system 140.

Furthermore, it is noted that the functionality described in connection with the flowcharts described herein can be implemented as special-function and/or configured general-function hardware modules, portions of program code executed by a processor (e.g., the processor 113 in the computer system 112) for achieving specific logical functions, determinations, and/or steps described in connection with the flowcharts. Where used, program code can be stored on any type of computer readable medium (e.g., computer readable storage medium or non-transitory media, such as data storage 114 described above with respect to computer system 112), for example, such as a storage device including a disk or hard drive. In addition, each block of the flowcharts can represent circuitry that is wired to perform the specific logical functions in the process. Unless specifically indicated, functions in the flowcharts can be executed out of order from that shown or discussed, including substantially concurrent execution of separately described functions, or even in reverse order in some examples, depending on the functionality involved, so long as the overall functionality of the described method is maintained. Furthermore, similar combinations of hardware and/or software elements can be employed to implement the methods described in connection with other flowcharts provided in the present disclosure.

As used herein a "scanning zone" generally refers to a region of a scanned environment scanned by a single LIDAR device, or a combination of LIDAR devices, that is completely sampled in a complete scan by the LIDAR device. That is, for a LIDAR device operated to continuously actively map its surroundings for reflective features, the scanning zone is the complete region mapped before returning to map the same point again. Generally, the scanning zone referred to herein is defined with reference to the point of view of the LIDAR device in terms of azimuth (e.g., angle along the horizon) and altitude (e.g., angle perpendicular to the horizon) with respect to the point of view of the LIDAR device. Thus, the geographic location mapped by the scanning zone of a LIDAR device is not fixed, but rather moves with the LIDAR device. For example, the scanning zone can be considered a bubble surrounding a particular LIDAR device with dimensions defined by the maximum distance sensitivity of the LIDAR device.

In some embodiments, a single laser in the LIDAR device (e.g., the LIDAR device 302 discussed in connection with FIGS. 3A-3C) can have a scanning range of approximately 150 meters distance, a thirty degree vertical ("altitude") field of view, and approximately a thirty degree horizontal ("azimuth") field of view. Additional lasers included in the LIDAR device can have complementary ranges and fields of view as well so as to provide sufficient coverage of an environmental scene to inform navigational determinations. In some embodiments, the azimuth range of the scanning zone can be approximately 360 degrees, or a divisor thereof, such as 180, 90, 60, etc. to allow for 360 degree coverage by an even number of similar such LIDAR devices. In some embodiments, the altitude range can extend from 0 to 180 degrees. In some embodiments, the altitude range of the scanning zone can extend by an approximately equal number of degrees to either side of the horizon, such as 30 degrees either side of the horizon (60 to 120 degrees altitude), 20 degrees either side of the horizon (70 to 110 degrees altitude), etc. Of course, the altitude range can also be an incomplete coverage of the available 0 to 180 degree range that is biased above or below the horizon, such as providing coverage up to 45 degrees above the horizon and 15 degrees below the horizon (45 to 105 degrees altitude), to take just one example. Of course, as with the azimuth ranges, the altitude ranges can be divided substantially equally between multiple LIDAR devices, such as in 30 degree sections, 20 degree sections, 15 degree sections, etc.

Furthermore, a complete scan is referred to herein as being completed within a scanning interval, which can be the time required for performing a complete scan of the scanning zone. In other words, a given point in the scanning zone is generally scanned on an interval given by the scanning interval, with every other point in the scanning zone being scanned in the interim.

Figure 9:
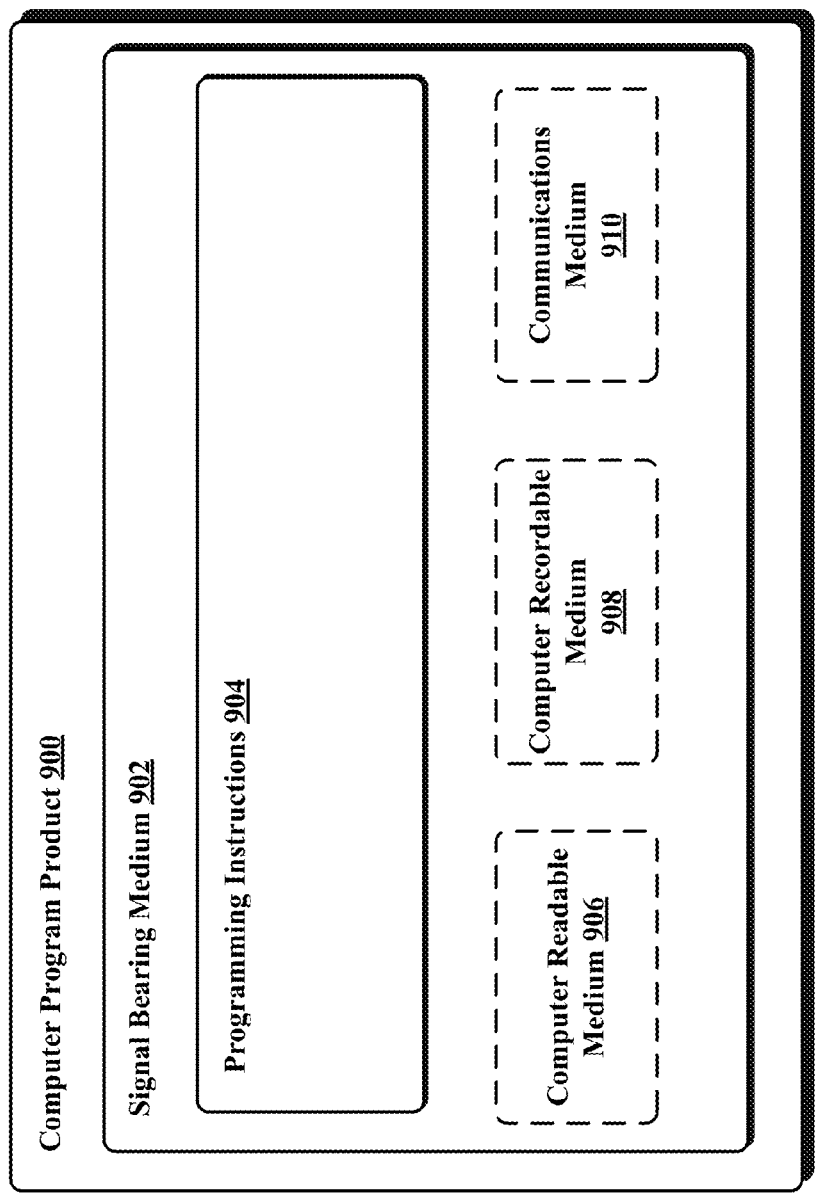
FIG. 9 depicts a computer-readable medium configured according to an example embodiment.

FIG. 9 depicts a computer-readable medium configured according to an example embodiment. In example embodiments, the example system can include one or more processors, one or more forms of memory, one or more input devices/interfaces, one or more output devices/interfaces, and machine-readable instructions that when executed by the one or more processors cause the system to carry out the various functions, tasks, capabilities, etc., described above.

As noted above, in some embodiments, the disclosed techniques can be implemented by computer program instructions encoded on a non-transitory computer-readable storage media in a machine-readable format, or on other non-transitory media or articles of manufacture (e.g., the instructions 115 stored on the data storage 114 of the computer system 112 of vehicle 100). FIG. 9 is a schematic illustrating a conceptual partial view of an example computer program product that includes a computer program for executing a computer process on a computing device, arranged according to at least some embodiments presented herein.

In one embodiment, the example computer program product 900 is provided using a signal bearing medium 902. The signal bearing medium 902 may include one or more programming instructions 904 that, when executed by one or more processors may provide functionality or portions of the functionality described above with respect to FIGS. 1-8. In some examples, the signal bearing medium 902 can be a computer-readable medium 906, such as, but not limited to, a hard disk drive, a Compact Disc (CD), a Digital Video Disk (DVD), a digital tape, memory, etc. In some implementations, the signal bearing medium 902 can be a computer recordable medium 908, such as, but not limited to, memory, read/write (R/W) CDs, R/W DVDs, etc. In some implementations, the signal bearing medium 902 can be a communications medium 910, such as, but not limited to, a digital and/or an analog communication medium (e.g., a fiber optic cable, a waveguide, a wired communications link, a wireless communication link, etc.). Thus, for example, the signal bearing medium 902 can be conveyed by a wireless form of the communications medium 910.

The one or more programming instructions 904 can be, for example, computer executable and/or logic implemented instructions. In some examples, a computing device such as the computer system 112 of FIG. 1 is configured to provide various operations, functions, or actions in response to the programming instructions 904 conveyed to the computer system 112 by one or more of the computer readable medium 906, the computer recordable medium 208, and/or the communications medium 910.

The non-transitory computer readable medium could also be distributed among multiple data storage elements, which could be remotely located from each other. The computing device that executes some or all of the stored instructions could be a vehicle, such as the vehicle 200 illustrated in FIG. 2. Alternatively, the computing device that executes some or all of the stored instructions could be another computing device, such as a server.

While various example aspects and example embodiments have been disclosed herein, other aspects and embodiments will be apparent to those skilled in the art. The various example aspects and example embodiments disclosed herein are for purposes of illustration and are not intended to be limiting, with the true scope and spirit being indicated by the following claims.

The invention claimed is:

1. A method comprising:
causing a light detection and ranging (LIDAR) device associated with an autonomous vehicle to scan through a scanning zone while emitting light pulses;
determining a three-dimensional (3-D) point map of the scanning zone based on time delays between emitting the light pulses and receiving corresponding returning reflected signals and based on orientations of the LIDAR device while emitting the light pulses;
identifying a region of the scanning zone for spectral analysis based on the 3-D point map including a particular reflective feature that resembles a type of non-solid object;
imaging, with a hyperspectral sensor associated with the autonomous vehicle, the identified region of the scanning zone so as to generate spectral information characterizing a spectral distribution of radiation received from the particular reflective feature;
correlating the particular reflective feature with a non-solid material based on the spectral distribution of radiation received from the particular reflective feature including one or more spectral characteristics of the non-solid material;
in response to the correlating, determining that the particular reflective feature corresponds to a non-solid object;
combining information from the LIDAR device and the hyperspectral sensor, wherein the hyperspectral sensor is separate from the LIDAR device, and wherein the combined information indicates whether reflective features in the 3-D point map correspond to solid objects or non-solid objects;
analyzing the combined information to identify obstacles relative to a current path of the autonomous vehicle;
determining a modified path of the autonomous vehicle that avoids the identified obstacles; and
controlling the autonomous vehicle to navigate along the modified path.

2. The method according to claim 1, wherein the particular reflective feature resembles an exhaust plume, and wherein the non-solid material correlated with the particular reflective feature comprises carbon monoxide.

3. The method according to claim 1, wherein the particular reflective feature resembles a water spray pattern, and wherein the non-solid material correlated with the particular reflective feature comprises water or water vapor.

4. The method according to claim 1, wherein the hyperspectral sensor is configured to detect radiation with wavelengths between 400 nm and 2500 nm.

5. The method according to claim 1, wherein the LIDAR device is configured to complete a scan of the entire scanning zone during a scanning interval, and wherein the imaging the region is initiated during the scanning interval based on information indicative of returning reflected signals received during one or more previous scanning intervals.

6. An autonomous vehicle system comprising:
a light detection and ranging (LIDAR) device including:
a light source configured to be scanned through a scanning zone while emitting light pulses; and a light detector configured to receive returning reflected signals from reflective features in the scanning zone, if any;

a hyperspectral sensor configured to image selected regions of the scanning zone and to characterize spectral distributions of radiation received from the imaged regions, wherein the hyperspectral sensor is separate from the LIDAR device; and a controller configured to:

cause the LIDAR device to scan the scanning zone while emitting light pulses;

receive information from the LIDAR device indicative of the time delays between the emission of the light pulses and the reception of corresponding returning reflected signals;

determine, based on the time delays and orientations of the LIDAR device while emitting the light pulses, a three dimensional (3-D) point map;

identify a region of the scanning zone for spectral analysis based on the 3-D point map including a particular reflective feature that resembles a type of non-solid object;

cause the hyperspectral sensor to image the identified region of the scanning zone;

receive, from the hyperspectral sensor, spectral information characterizing a spectral distribution of radiation received from the particular reflective feature;

correlate the particular reflective feature with a non-solid material based on the spectral distribution of radiation received from the particular reflective feature including one or more spectral characteristics of the non-solid material;

in response to the correlating, determining that the particular reflective feature corresponds to a non-solid object;

combining information from the LIDAR device and the hyperspectral sensor, wherein the combined information indicates whether reflective features in the 3-D point map correspond to solid objects or non-solid objects;

analyze the combined information to identify obstacles relative to a current path of the autonomous vehicle;

determine a modified path of the autonomous vehicle that avoids the identified obstacles; and control the autonomous vehicle to navigate along the modified path.

7. The autonomous vehicle system according to claim 6, wherein the particular reflective feature resembles an exhaust plume, and wherein the non-solid material correlated with the particular reflective feature comprises carbon monoxide.

8. The autonomous vehicle system according to claim 6, wherein the particular reflective feature resembles a water spray pattern, and wherein the non-solid material correlated with the particular reflective feature comprises water or water vapor.

9. A computer readable medium storing instructions that, when executed by one or more processors in a computing device, cause the computing device to perform operations, the operations comprising:

scanning a light detection and ranging (LIDAR) device associated with an autonomous vehicle through a scanning zone while emitting light pulses;

determining a three-dimensional (3-D) point map of the scanning zone based on time delays between emitting the light pulses and receiving corresponding returning reflected signals and based on orientations of the LIDAR device while emitting the light pulses;

identifying a region of the scanning zone for spectral analysis based on the 3-D point map including a particular reflective feature that resembles a type of non-solid object;

imaging, with a hyperspectral sensor associated with the autonomous vehicle, the identified region of the scanning zone so as to generate spectral information characterizing a spectral distribution of radiation received from the particular reflective feature;

correlating the particular reflective feature with a non-solid material based on the spectral distribution of radiation received from particular reflective feature including one or more spectral characteristics of the non-solid material;

in response to the correlating, determining that the particular reflective feature corresponds to a non-solid object;

combining information from the LIDAR device and the hyperspectral sensor, wherein the hyperspectral sensor is separate from the LIDAR device, and wherein the combined information indicates whether reflective features in the 3-D point map correspond to solid objects or non-solid objects;

analyzing the combined information to identify obstacles relative to a current path of the autonomous vehicle;

determining a modified path of the autonomous vehicle that avoids the identified obstacles; and controlling the autonomous vehicle to navigate along the modified path.

10. The computer readable medium according to claim 9, wherein the particular reflective feature resembles an exhaust plume, and wherein the non-solid material correlated with the particular reflective feature comprises carbon monoxide.

11. The computer readable medium according to claim 9, wherein the particular reflective feature resembles a water spray pattern, and wherein the non-solid material correlated with the particular reflective feature comprises water or water vapor.

12. The method according to claim 1, wherein the imaging with the hyperspectral sensor occurs in response to identifying the region of the scanning zone for spectral analysis.

13. The method according to claim 1, wherein the hyperspectral sensor outputs a pixelated image in which each pixel includes intensity values for multiple spectral bands.

14. The method according to claim 13, further comprising correlating a location of the particular reflective feature in the 3-D point map with a corresponding location of the particular reflective feature in the pixelated image.

15. The autonomous vehicle system according to claim 6, wherein the controller is configured to cause the hyperspectral sensor to image the identified region of the scanning zone in response to identifying the region of the scanning zone for spectral analysis.

16. The autonomous vehicle system according to claim 6, wherein the hyperspectral sensor outputs a pixelated image in which each pixel includes intensity values for multiple spectral bands.

17. The autonomous vehicle system according to claim 16, wherein the controller is further configured to correlate a location of the particular reflective feature in the 3-D point map with a corresponding location of the particular reflective feature in the pixelated image.

18. The computer readable medium according to claim 9, wherein the imaging with the hyperspectral sensor occurs in response to identifying the region of the scanning zone for spectral analysis.

19. The computer readable medium according to claim 9, wherein the hyperspectral sensor outputs a pixelated image in which each pixel includes intensity values for multiple spectral bands.

20. The computer readable medium according to claim 19, wherein the operations further comprise correlating a location of the particular reflective feature in the 3-D point map with a corresponding location of the particular reflective feature in the pixelated image.

\* \* \* \* \*